US006749632B2

(12) United States Patent
Sandstedt et al.

(10) Patent No.: US 6,749,632 B2
(45) Date of Patent: Jun. 15, 2004

(54) APPLICATION OF WAVEFRONT SENSOR TO LENSES CAPABLE OF POST-FABRICATION POWER MODIFICATION

(75) Inventors: Christian A. Sandstedt, Pasadena, CA (US); Jagdish M. Jethmalani, Pasadena, CA (US); Robert H. Grubbs, South Pasadena, CA (US); Julia A. Kornfield, Pasadena, CA (US); Daniel M. Schwartz, San Francisco, CA (US); Robert Maloney, Pacific Palisades, CA (US)

(73) Assignees: California Institute of Technology, Pasadena, CA (US); The Regents of the University of California, Oakland, CA (US); Calhoun Vision, Inc., Pasadena, CA (US)

( * ) Notice: Subject to any disclaimer, the term of this patent is extended or adjusted under 35 U.S.C. 154(b) by 0 days.

(21) Appl. No.: 09/813,598

(22) Filed: Mar. 20, 2001

(65) Prior Publication Data
US 2002/0016629 A1 Feb. 7, 2002

Related U.S. Application Data
(60) Provisional application No. 60/190,738, filed on Mar. 20, 2000.

(51) Int. Cl.[7] .................................................. A61F 2/16
(52) U.S. Cl. ...................................... 623/6.22; 623/6.56
(58) Field of Search ................................ 623/4.1, 5.11, 623/5.14, 6.18–6.32, 6.56–6.63; 351/205, 206–216

(56) References Cited

U.S. PATENT DOCUMENTS

| 3,955,015 A | 5/1976 | Ohtsuka et al. |
| 4,104,204 A | 8/1978 | Williams |
| 4,173,474 A | 11/1979 | Tanaka et al. |
| 4,173,475 A | 11/1979 | Chandross et al. |
| 4,260,725 A | 4/1981 | Keogh et al. |
| 4,330,383 A | 5/1982 | Ellis et al. |
| 4,575,373 A | 3/1986 | Johnson |
| 4,685,921 A | 8/1987 | Peyman |
| 4,787,903 A | 11/1988 | Grendahl |
| 4,790,847 A | 12/1988 | Woods |
| 4,816,031 A | 3/1989 | Pfoff |
| 4,846,172 A | 7/1989 | Berlin |
| 4,921,589 A | 5/1990 | Yates et al. |
| 4,942,112 A | 7/1990 | Monroe et al. |
| 5,066,301 A | 11/1991 | Wiley |
| 5,141,678 A | 8/1992 | Blum |
| 5,171,266 A | 12/1992 | Wiley et al. |
| 5,173,381 A | 12/1992 | Natansohn et al. |
| 5,213,825 A | 5/1993 | Shimizu et al. |

(List continued on next page.)

FOREIGN PATENT DOCUMENTS

| DE | 3605512 A1 | 8/1986 |
| EP | 042384 A3 | 2/1992 |
| EP | 0472384 A2 | 2/1992 |

(List continued on next page.)

OTHER PUBLICATIONS

International Preliminary Examination Report dated Jul. 16, 2002 for corresponding International Application No. PCT/US01/09276, 9 pgs.

(List continued on next page.)

Primary Examiner—David H. Willse
Assistant Examiner—Hieu Phan
(74) Attorney, Agent, or Firm—Christie, Parker & Hale, LLP

(57) ABSTRACT

The present invention relates to methods of implementing an optical element having a refraction modulating composition. The methods include using a wavefront sensor to provide an optical measurement of the optical element. The present invention also relates to systems comprising an optical element having a refraction modulating composition and a wavefront sensor.

29 Claims, 10 Drawing Sheets

U.S. PATENT DOCUMENTS

| | | |
|---|---|---|
| 5,258,024 A | 11/1993 | Chavel et al. |
| 5,288,293 A | 2/1994 | O'Donnell, Jr. |
| 5,296,305 A | 3/1994 | Baude et al. |
| 5,443,506 A | 8/1995 | Garabet |
| 5,470,662 A | 11/1995 | Weber et al. |
| 5,480,428 A | 1/1996 | Fedorov et al. |
| 5,529,861 A | 6/1996 | Redfield |
| 5,549,668 A | 8/1996 | O'Donnell, Jr. |
| 5,623,002 A | 4/1997 | Nomura et al. |
| 5,684,636 A | 11/1997 | Chow et al. |
| 5,702,846 A | 12/1997 | Sato et al. |
| 5,725,575 A | 3/1998 | O'Donnell, Jr. |
| 5,728,155 A | 3/1998 | Anello et al. |
| 5,728,156 A | 3/1998 | Gupta et al. |
| 5,744,267 A | 4/1998 | Meerholz et al. |
| 5,762,836 A | 6/1998 | Bos et al. |
| 5,807,906 A | 9/1998 | Bonvallot et al. |
| 5,858,585 A | 1/1999 | Haarer et al. |
| 5,892,601 A | 4/1999 | Curtis et al. |
| 5,920,536 A | 7/1999 | Campbell et al. |
| 5,943,145 A | 8/1999 | Curtis et al. |
| 5,949,521 A * | 9/1999 | Williams et al. ............ 351/246 |
| 5,964,802 A | 10/1999 | Anello et al. |
| 5,984,962 A | 11/1999 | Anello et al. |
| 5,995,251 A | 11/1999 | Hesselink et al. |
| 5,998,096 A | 12/1999 | Umemoto et al. |
| 6,046,290 A | 4/2000 | Berneth et al. |
| 6,154,432 A | 11/2000 | Faruqi et al. |
| 6,271,281 B1 | 8/2001 | Liao et al. |
| 6,450,642 B1 * | 9/2002 | Jethmalani et al. ......... 351/219 |

FOREIGN PATENT DOCUMENTS

| | | |
|---|---|---|
| EP | 0689067 A2 | 12/1995 |
| JP | 60175009 | 9/1985 |
| JP | 61027501 | 2/1986 |
| JP | 05096553 | 4/1993 |
| JP | 07281426 | 10/1995 |
| JP | 08101499 | 4/1996 |
| JP | 08101502 | 4/1996 |
| JP | 08101503 | 4/1996 |
| JP | 11202740 | 7/1999 |
| WO | WO-93/21245 A1 | 10/1993 |
| WO | WO-95/17460 A1 | 6/1995 |
| WO | WO-98/05272 A1 | 2/1998 |
| WO | WO-98/27863 A1 | 7/1998 |
| WO | WO-99/26112 A1 | 5/1999 |
| WO | WO-00/41650 A1 | 7/2000 |
| WO | WO-01/21061 A1 | 3/2001 |
| WO | WO-01/71411 A2 | 9/2001 |
| WO | WO-01/86647 A3 | 11/2001 |
| WO | WO-01/86647 A2 | 11/2001 |

OTHER PUBLICATIONS

PCT International Search Report dated Nov. 29, 2001 from corresponding International Application No. PCT/US01/09276 filed Mar. 20, 2001.

American National Standard for Safe Use of Lasers; 8. Criteria for Exposures of Eye and Skin; American National Standard; 1993; pp. 31–43; Laser Institute of America; Orlando, Florida.

Holographic Optical Elements, National Technical Information Service Publication AD760561, Jan. 1973., 170 pages, U.S. Department of Commerce.

Allen et al., Synthesis, photopolymerization and photochemistry of novel polysiloxane photoinitiators; J. Photochem. Photobiol. A: Chem.; 1991; pp. 125–139; vol. 62; Elsevier Sequoia, Lausanne.

Apple et al., Irreversible Silicone Oil Adhesion to Silicone Intraocular Lenses—A Clinicopathologic Analysis; Ophthalmology; Oct. 1996; pp. 1555–1562; vol. 103; No. 10.

Baltus et al., Solubility and Diffusivity of Cyclic Oligomers in Poly(dimethylsiloxane) Using Capillary Column Inverse Gas Chromatography; Macromolecules; 1993; pp. 5651–5656; vol. 26; American Chemical Society.

Barakat; General Diffraction Theory of Optical Aberration Tests, from the Point of View of Spatial Filtering; Journal of the Optical Society of America; Nov. 1969; pp. 1432–1439; vol. 59; No. 11.

Bennett et al.; Clinical Visual Optics—3rd Edition, Chapters 4 & 5; 1998; pp. 62–92; Butterworth–Heinemann Ltd.; Woburn, Massachusetts.

Brandser et al., Accuracy of IOL calculation in cataract surgery; Acta Opthalmologica Scandinavica; 1997; pp. 162–165; vol. 75; No. 2.

Bräuchle et al., Holographic Spectroscopy and Holographic Information Recording in Polymer Matrices; Lasers in Polymer Science and Technology: Applications; 1990; pp. 181–209; vol. III, Ed. Jean–Pierre Fouassier, Jan. F. Rabek, CRC Press.

Canabal et al., Automatic processing in moiré deflectometry by local fringe direction calculation; Applied Optics; Sep. 1, 1998; pp. 5894–5901; vol. 37, No. 2; Optical Society of America.

Chang et al., An Improved Technique of Measuring the Focal Length of a Lens; Optics Communications; Oct. 15, 1989; pp. 257–262; vol. 73, No. 4; Elsevier Science Publishers B.V., North Holland.

Cornejo et al., Ronchi Test of Aspherical Surfaces, Analysis, and Accuracy; Applied Optics; Aug. 1970; pp. 1897–1901; vol. 9, No. 8.

Cornejo–Rodriguez; 9/Ronchi Test; Optical Shop Testing, 2nd Ed.—Malacara–Doblado, D.; 1992, pp. 321–365; John Wiley & Sons, Inc., New York.

Decker et al., High–Speed Polymerization of Acrylate Monomers by UV Irradiation; pp. 487–488.

Dress et al.; Volume Phase Gratings in DMPA–Doped Polymers; Applied Physics A; 1994; vol. 58; pp. 401–405;Springer–Verlag.

Ducharme et al., Observation of the Photorefractive Effect in a Polymer, Physical Review Letters, Apr. 8, 1991, pp. 1846–1849, vol. 66, No. 14, American Physical Society.

Duke–Elder et al., System of Ophthalmology—Ophthalmic Optics and Refraction, Chapters II–IV, 1970, pp. 26–153, vol. V, Henry Kimpton, London.

Fouassier et al., Photopolymers for laser imaging and holographic recording: design and reactivity of photosensitizers; Optical Engineering; Jan. 1996; vol. 35, No. 1, pp. 304–312.

Fouassier et al., Visible Lasers Lights in Photoinduced Polymerization. VI. Thioxanthones and Ketocoumarins as Photoinitiators; Journal of Applied Polymer Science; 1992; vol. 44; pp. 1779–1786; John Wiley & Sons, Inc.

Gedde et al., Sorption of Low Molar Mass Silicones in Silicone Elastomers; Polymer Engineering and Science; Aug. 1996, vol. 36, No. 16; pp. 2077–2082.

Goodman, Chapter 8/Wavefront–Reconstruction Imaging, or Holography, Introduction to Fourier Optics, 1968, pp. 198–273, McGraw–Hill, Inc., USA.

He et al., Chain Extension of $\alpha,\omega$–Dihydroxy Polydimethylsiloxane: Simulation of the Linear Polycondensation Reaction; European Polymer Journal; 1991; pp. 449–453; vol. 27, No. 4/5; Pergamon Press plc; Great Britain.

He et al., Competition Between Polycondensation of α,ω–Dihydroxy Polydimethysiloxane and its Condensation with Alkoxy Silane: A Kinetic Approach; European Polymer Journal; 1988; pp. 1145–1148; vol. 24, No. 12; Pergamon Press plc; Great Britain.

Ingwall et al., Hologram recording with a new photopolymer system; Optical Engineering; Oct. 1985; pp. 808–811; vol. 24, No. 5; Society of Photo–Optical Instrumentation Engineers.

Ingwall et al.; Mechanism of hologram formation in DMP–128 photopolymer; Optical Engineering; Jun. 1989; pp. 586–591; vol. 28, No. 6; Society of Photo–Optical Instrumentation Engineers.

Javitt et al., Outcomes of Cataract Extraction with Multifocal Intraocular Lens Implantation—Functional Status of Quality of Life; Ophthalmology; Apr. 1997; pp 589–599; vol. 104; No. 4.

Kippelen et al., New highly efficient photorefractive polymer composite for optical–storage and image–processing applications, Electronics Letters, Oct. 14, 1993, pp. 1873–1874, vol. 29, No. 21.

Kloosterboer; Network Formation by Chain Crosslinking Photopolymerization and its Applications in Electronics; Advances in Polymer Science 84; 1988; pp. 1–61; Springer–Verlag Berlin Heidelberg.

Kunzler; Silicone Hydrogels for Contact Lens Application, Trends in Polymer Science; Feb. 1996; vol. 4, No. 2; pp. 52–59; Elsevier Science Ltd.

Kunzler et al.; Hydrogels Based on Hydrophilic Side–Chain Siloxanes; Journal of Applied Polymer Science; 1995; vol. 55; pp. 611–619; John Wiley & Sons, Inc.

Lai et al., Synthesis and Characterization of α, ω–Bis(4–hydroxybutyl)Polydimethylsiloxanes; Journal of Polymer Science; 1995; vol. 33; pp. 1773–1782; John Wiley & Sons, Inc.

Leaming, Practice styles and preferences of ASCRS members—1996 survey.; J. Cataract Refract. Surg.; May 1997; pp. 527–535; vol. 23; ASCRS and ESCRS; Elsevier Science Inc.

Leaming, *special report*—Practice styles and preferences of ASCRS members—1999 survey.; J. Cataract Refract. Surg.; Jun. 2000; pp. 913–921; vol. 26; ASCRS and ESCRS; Elsevier Science Inc.

Levi, New Compound Brightens Outlook for Photorefractive Polymers, Physics Today, Jan. 1995, pp. 17–19, vol. 48, No. 1, American Institute of Physics.

Liang et al., Objective measurement of wave aberrations of the human eye with the use of a Hartmann–Shack wavefront sensor, J. Optical Society of America, Jul. 1994, pp. 1949–1957, vol. 11, No. 7, Optical Society of America.

Liang et al., Supernormal vision and high–resolution retinal imaging through adaptive optics, J. Optical Society of America, Nov. 1997, pp. 2884–2892, vol. 14, No. 11, Optical Society of America.

Longhurst; Chapter II—The General Geometrical Theory of Optical Systems; Geometrical and Physical Optics—2nd Edition; 1967; pp. 16–41; John Wiley & Sons Inc., New York, N.Y.

Longhurst; Chapter XV—The Monochromatic Aberrations; Geometrical and Physical Optics—2nd Edition; 1967; pp. 340–355; John Wiley & Sons Inc., New York, N.Y.

Malacara–Doblado; Measuring the curvature of spherical wavefronts with Talbot interferometry; Optical Engineering; vol. 36, No. 7; Jul. 1997; pp. 2016–2024.

Malacara et al.; Null Ronchi Test for Aspherical Surfaces; Applied Optics; Aug. 1974; pp. 1778–1780; vol. 13, No. 8.

Manivannan et al.; Trends in Holographic Recording Materials; Trends in Polymer Science; Aug. 1994; vol. 2, No. 8; pp. 282–290; Elsevier Science Ltd.

Meerholz et al.; A photorefractive polymer with high optical gain and diffraction efficiency near 100%, Letters to Nature, Oct. 6, 1994, pp. 497–500, vol. 371.

Mendívil, Intraocular lens implantation through 3.2 versus 4.0 mm incisions; J. Cataract Refract. Surg.; Dec. 1996; pp. 1461–1464; vol. 22; No. 10.

Merker et al., The Copolymerization of Cyclic Siloxanes, Journal of Polymer Science; 1960; vol. XLIII; pp. 297–310.

Moerner et al., Photorefractive Polymers for Holographic Optical Storage, OSA Technical Digest Series, 1995, pp. 330–333, vol. 21.

Moerner et al., Polymeric Photorefractive Materials; Chemical Reviews 1994; pp. 127–155; vol. 94; American Chemical Society.

Monroe; Photoinitiators for Free–Radical–Initiated Photoimaging Systems; Chemical Reviews; 1993, vol. 93, No. 1; pp. 435–448; American Chemical Society.

Nakano et al.; Talbot interferometry for measuring the focal length of a lens; Applied Optics; Oct. 1, 1985; pp. 3162–3166; vol. 24, No. 19; Optical Society of America.

Negishi et al.; Evaluation of a Zonal–progressive Multifocal Intraocular Lens; American Journal of Ophthalmology; Sep. 1997; pp. 321–330; vol. 124; No. 3; American Journal of Ophthalmology.

Olsen, Sources of error in intraocular lens power calculation; J. Cataract Refract. Surg.; Mar. 1992; pp. 125–129; vol. 18; No. 2.

Olsen et al., Accuracy of the newer generation intraocular lens power calculation formulas in long and short eyes; J. Cataract Refract. Surg.; Mar. 1991; pp. 187–193; vol. 17; No. 2.

Oshika et al., Three year prospective, randomized evaluation of intraocular lens implantation through 3.2 and 5.5 mm incisions; J. Cataract Refract Surg.; Apr. 1998; pp. 509–514; vol. 24.

Pierro et al.; Clinical variability in keratometry, ultrasound biometry measurements, and emmetropic intraocular lens power calculation; J. Cataract Refract. Surg.; Jan. 1991; pp. 91–94; vol. 17; No. 1.

Poga et al.; High Efficiency Photorefractive Polymer with Immunity to Crystallization, OSA Technical Digest Series, 1995, pp. 342–345, vol. 21.

Pouliquen et al., Functionalized Polysiloxanes with Thioxanthone Side Groups: A Study of Their Reactivity as Radical Polymerization Macroinitiators; Macromolecules; 1995; pp. 8028–8034; vol. 28; American Chemical Society.

Ravalico et al., Postoperative Cellular Reaction on Various Intraocular Lens Materials; Ophthalmology; Jul. 1997; pp. 1084–1091; vol. 104; No. 7.

Riffle et al.; 2/Elastomeric Polysiloxane Modifiers for Epoxy Networks—Synthesis of Functional Oligomers and Network Formation Studies; Epoxy Resin Chemistry; 1983; pp. 21–54.

Rigbi et al.; Concurrent Chain Extension and Crosslinking of Hydroxyl–Terminated Poly(dimethyl siloxane): Possible Formation of Catenate Structures; Journal of Polymer Science: Polymer Physics Edition; 1986; pp. 443–449; vol. 24, No. 2; John Wiley & Sons, Inc.

Sawhney et al.; Bioerodible Hydrogels Based on Photopolymerized Poly(ethylene glycol)–co–poly(α–hydroxy acid) Diacrylate Macromers; Macromolecules; 1993; pp. 581–587; vol. 26; American Chemical Society.

Smothers et al., Hologram Recording in Dupont's New Photopolymer Materials; IEE Conference Publication; 1989, pp. 184–189; vol. 311.

Smothers et al., Photopolymers for holography; Practical Holography IV; 1990; pp. 20–29; vol. 1212; SPIE.

Steinert et al.; Long–term clinical results of AMO PhacoFlex model SI–18 intraocular lens implantation; J. Cataract Refract. Surg.; May 1995; pp. 331–338; vol. 21; No. 3.

Su et al., A new technique for measuring the effective focal length of a thick lens or a compound lens; Optics Communications; Aug. 15, 1990; pp. 118–122; vol. 78, No. 2; Elsevier Science Publishers B.V.; North Holland.

Tanabe et al., Visible Light Photopolymerization: Synthesis of New Fluorone Dyes and Photopolymerization of Acrylic Monomers Using Them; Journal of Polymer Science: Part A: Polymer Chemistry; 1995; pp. 1691–1703; vol. 33; John Wiley & Sons, Inc.

* cited by examiner

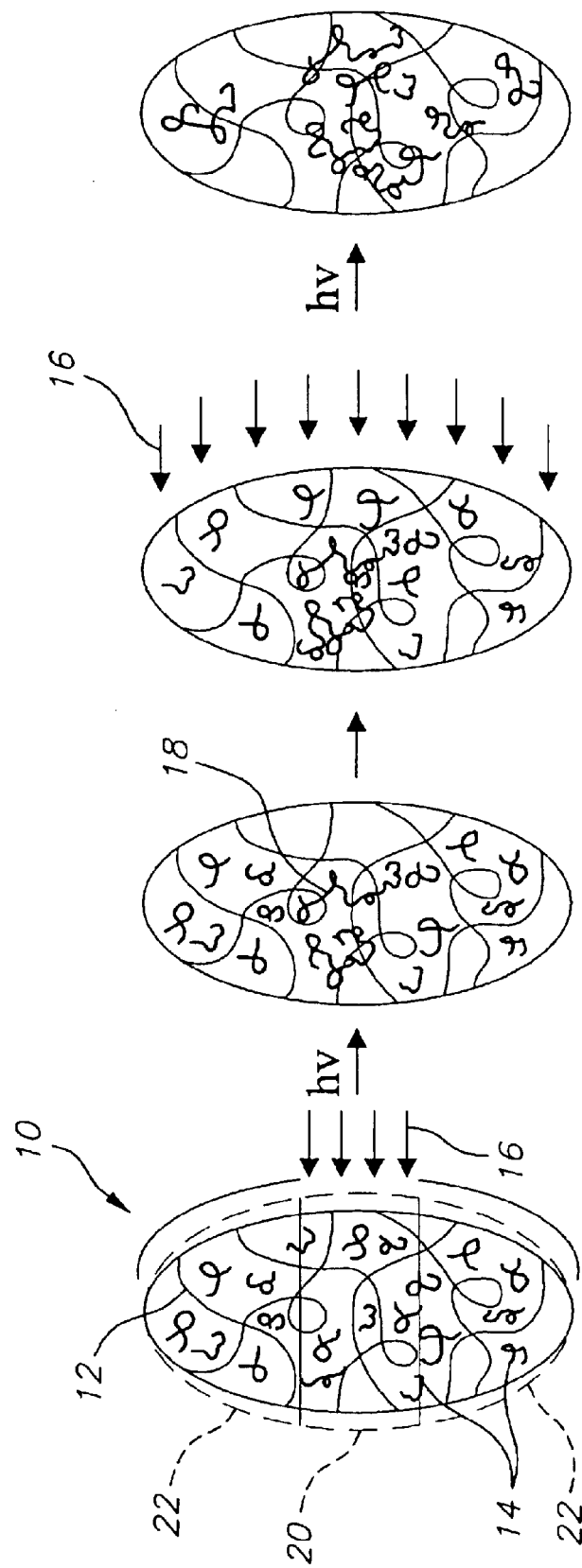

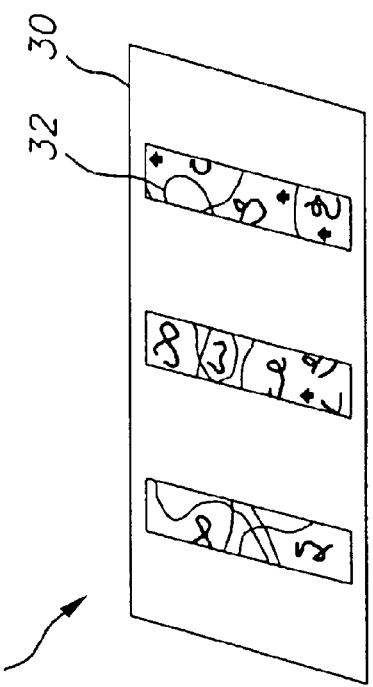
FIG. 2a
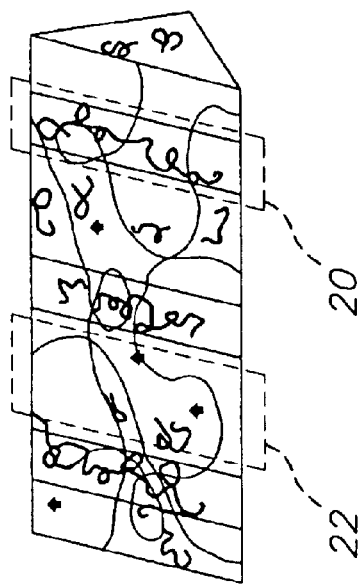
FIG. 2b
FIG. 2c
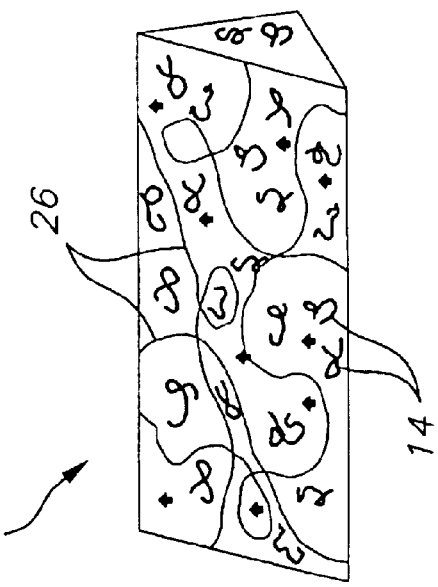
FIG. 2d

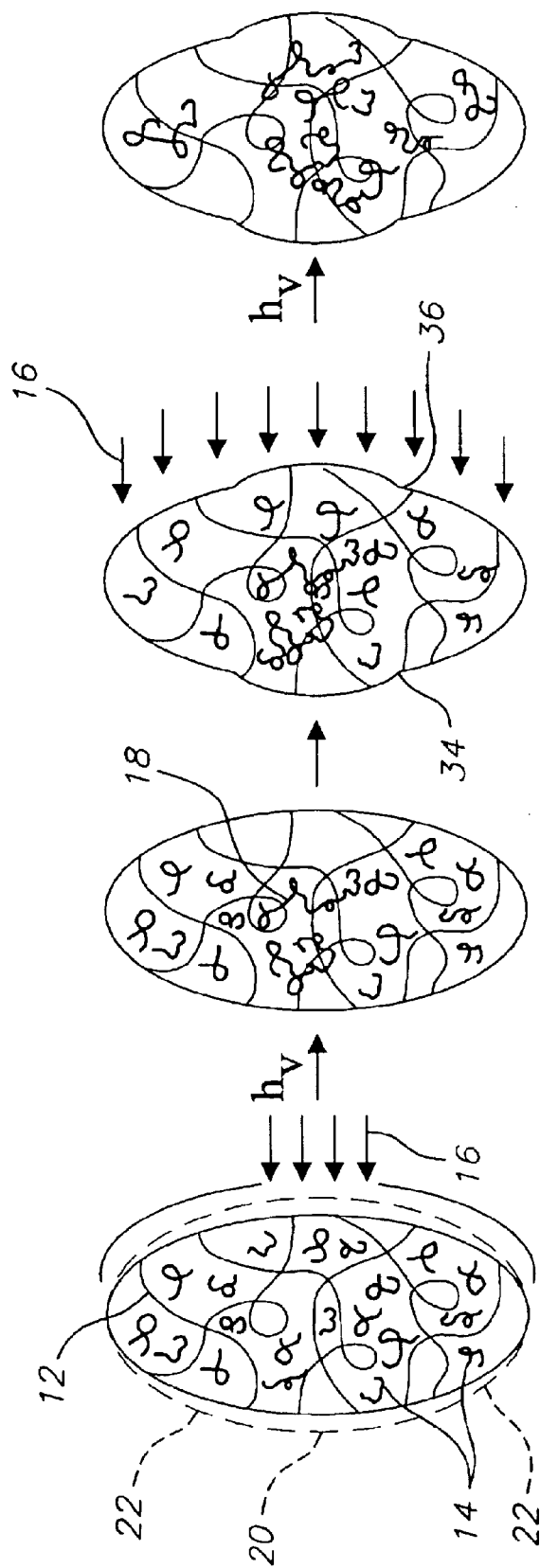

5 μm

APPLICATION OF WAVEFRONT SENSOR TO LENSES CAPABLE OF POST-FABRICATION POWER MODIFICATION

CROSS-REFERENCE TO RELATED APPLICATIONS

This is application is based on U.S. application Ser. No. 60/190,738, filed Mar. 20, 2000, the disclosure of which is incorporated by reference.

BACKGROUND

Approximately two million cataract surgery procedures are performed in the United States annually. The procedure generally involves making an incision in the anterior lens capsule to remove the cataractous crystalline lens and implanting an intraocular lens (IOL) in its place. In general, there are two types of intraocular lenses ("IOLs"). The first type of an IOL replaces the eye's natural lens. The most common reason for such a procedure is cataracts. The second type of IOL supplements the existing lens and functions as a permanent corrective lens. This type of lens (sometimes referred to as a phakic IOL) is implanted in the anterior or posterior chamber to correct any refractive errors of the eye. In theory, the power for either type of IOL required for emmetropia (i.e., perfect focus on the retina from light at infinity) can be precisely calculated. The power of the implanted lens is selected (based upon pre-operative measurements of ocular length and corneal curvature) to enable the patient to see without additional corrective measures (e.g., glasses or contact lenses). Unfortunately, due to errors in measurement, and/or variable lens positioning and wound healing; about half of all patients undergoing this procedure will not enjoy optimal vision without correction after surgery (Brandser et al., *Acta Ophthalmol Scand* 75:162–165 (1997); Oshika et al., *J cataract Refract Surg* 24:509–514 (1998)). Because the power of prior art IOLs generally cannot be adjusted once they have been implanted, the patient typically must be resigned to the use of additional corrective lenses such as glasses or contact lenses. Rarely, the implanted lens can be exchanged for another of more appropriate lens power.

In the last six to seven years there has been significant interest and advances in the use of wavefront sensing and adaptive optics techniques to measure and correct the aberrations present in the eye's optical system. Early studies were focused on nulling the optical aberrations of the eye to obtain high resolution images of the fundus (Liang et. al., *J. Opt. Soc. Am. A*, 14: 2884–2892 (1997); Liang et. al., *J Opt. Soc. Am. A*, 11: 1949–1957 (1994). Application of wavefront sensing to the eye has expanded to include preoperative aberration measurements of LASIK (Laser In Situ Keratomilcusis) and PRK (photorefractive keratotomy) patients (Seiler, $2^{nd}$ International Congress of Wavefront Sensing and Aberration-Free Refractive Correction, Feb. 10, 2001, Monterey, Calif.). The types of aberrations that dramatically reduce visual acuity include defocus, astigma6y7u765tism, spherical aberration, coma, and other higher order aberrations. The concept behind this procedure is that once the type, magnitude, and spatial distribution of the optical aberrations are measured across the eye, customized corneal ablation patterns can be generated that, in theory, would correct these aberrations to improve visual acuity. However, in practice, the corneal healing response of LASIK and PRK procedures cannot be predicted so the desired ablation pattern is not always achieved. In addition, post-LASIK and PRK patients complain of "halo" and glare effects during nighttime driving due to the sharp transition zone between the ablated and non-ablated regions of the cornea.

An IOL whose power may be adjusted after implantation and subsequent wound healing would be an ideal solution to post-operative refractive errors associated with cataract surgery, LASIK, and PRK. Moreover, such a lens would have wider applications and may be used to correct more typical conditions such as myopia, hyperopia, and astigmatism. In the later case, the IOL is called a phakic IOL. Although surgical procedures such as LASIK, which uses a laser to reshape the cornea, are available, only low to moderate myopia and hyperopia may be readily treated. In contrast, an IOL, functioning like glasses or contact lenses to correct for the refractive error of the natural eye, could be implanted in the eye of any patient. Because the power of the implanted lens may be adjusted, post-operative refractive errors due to measurement irregularities and/or variable lens positioning and wound healing may be corrected by fine tuning in-situ.

The present invention describes a post-operative, refraction adjustable IOL in combination with a wavefront sensor. This IOL could be inserted after cataract surgery to replace the cataractous lens or inserted into the eye without removing the natural crystalline lens, to correct for a preexisting optical conditions such as myopia, hyperopia, astigmatism, and/or other higher order terms. Once sufficient time has passed to allow for wound healing and refractive stabilization, the aberrations of the optical system containing the adjustable IOL can be measured with a wavefront sensor. Knowledge of the type, magnitude, and spatial distribution of these aberrations, in combination with the knowledge of the refractive adjustability of the material comprising the IOL (a treatment nomogram), will allow precise modification of the IOL to correct for the measured aberrations and thus achieve the desired, accurate IOL correction and optimal visual acuity.

SUMMARY

The present invention is directed in part to methods of implementing an optical element having a refraction modulating composition (RMC) dispersed in a polymer matrix. Applicants discovered that the RMC of an optical element, e.g., IOL, can be adjusted via polymerization based on the optical measurement obtained through a wavefront sensor such as the Shack-Hartmann wavefront sensor (also known as Hartmann-Shack wavefront sensor).

In one embodiment, then, the present invention is directed to an optical element and a wavefront sensor, wherein the optical element comprises a first polymer matrix composition (FPMC) and a RMC dispersed therein wherein the RMC is capable of stimulus-induced polymerization. In a particular embodiment the wavefront sensor is a Shack-Hartmann wavefront sensor.

In another embodiment, the present invention is directed to an optical element and an adaptive optics system, wherein the optical element comprises a FPMC and a RMC dispersed therein wherein the RMC is capable of stimulus-induced polymerization, wherein the adaptive optics system comprises a wavefront sensor and a wavefront compensator, such as a Shack-Hartmann wavefront sensor and a deformable mirror, a micro-electromechanical membrane, or a segmented micromirror wavefront compensator.

In yet another embodiment, the optical element is an IOL. In such an embodiment the FPMC can be made of any suitable polymer, such as a polysiloxane.

In still another embodiment the invention is directed to a method of implementing an optical element having a RMC dispersed therein. The method comprising obtaining an optical measurement of the optical element with a wavefront sensor, and inducing an amount of polymerization of the RMC, wherein the amount of polymerization is determined by the optical measurement. In this embodiment any suitable optical aberration measurement can be utilized, such as measurements of optical path difference or wavefront tilts and ray tracing techniques. In such an embodiment the aberration measurement can measure any suitable aberrations coefficient, such as, for example, defocus, astigmatism, coma, spherical, and higher order aberrations.

In still yet another embodiment the invention is directed to a method of implementing an IOL implanted within an eye and having a RMC dispersed therein. The method comprising obtaining an optical measurement, with a wavefront sensor, of the eye implanted with the IOL and inducing an amount of polymerization of the RMC in the IOL, wherein the amount of polymerization is determined by the optical measurement.

BRIEF DESCRIPTIONS OF THE DRAWINGS

FIG. 1a is a schematic of a lens of the present invention being irradiated in the center followed by irradiation of the entire lens to "lock in" the modified lens power.

FIG. 1b is a schematic of a lens of the present invention being irradiated in the center followed by irradiation of the entire lens to "lock in" the modified lens power.

FIG. 1c is a schematic of a lens of the present invention being irradiated in the center followed by irradiation of the entire lens to "lock in" the modified lens power.

FIG. 1d is a schematic of a lens of the present invention being irradiated in the center followed by irradiation of the entire lens to "lock in" the modified lens power.

FIG. 2a illustrates the prism irradiation procedure that is used to quantify the refractive index changes after being exposed to various amounts of irradiation.

FIG. 2b illustrates the prism irradiation procedure that is used to quantify the refractive index changes after being exposed to various amounts of irradiation.

FIG. 2c illustrates the prism irradiation procedure that is used to quantify the refractive index changes after being exposed to various amounts of irradiation.

FIG. 2d illustrates the prism irradiation procedure that is used to quantify the refractive index changes after being exposed to various amounts of irradiation.

FIG. 5a is a schematic illustrating a second mechanism whereby the formation of the second polymer matrix modulates a lens property by altering lens shape.

FIG. 5b is a schematic illustrating a second mechanism whereby the formation of the second polymer matrix modulates a lens property by altering lens shape.

FIG. 5c is a schematic illustrating a second mechanism whereby the formation of the second polymer matrix modulates a lens property by altering lens shape.

FIG. 5d is a schematic illustrating a second mechanism whereby the formation of the second polymer matrix modulates a lens property by altering lens shape.

DETAILED DESCRIPTION OF THE PREFERRED EMBODIMENTS

The present invention relates generally to the application of wavefront sensing and correcting techniques to an optical element having a RMC dispersed in a polymer matrix.

Figure 9:
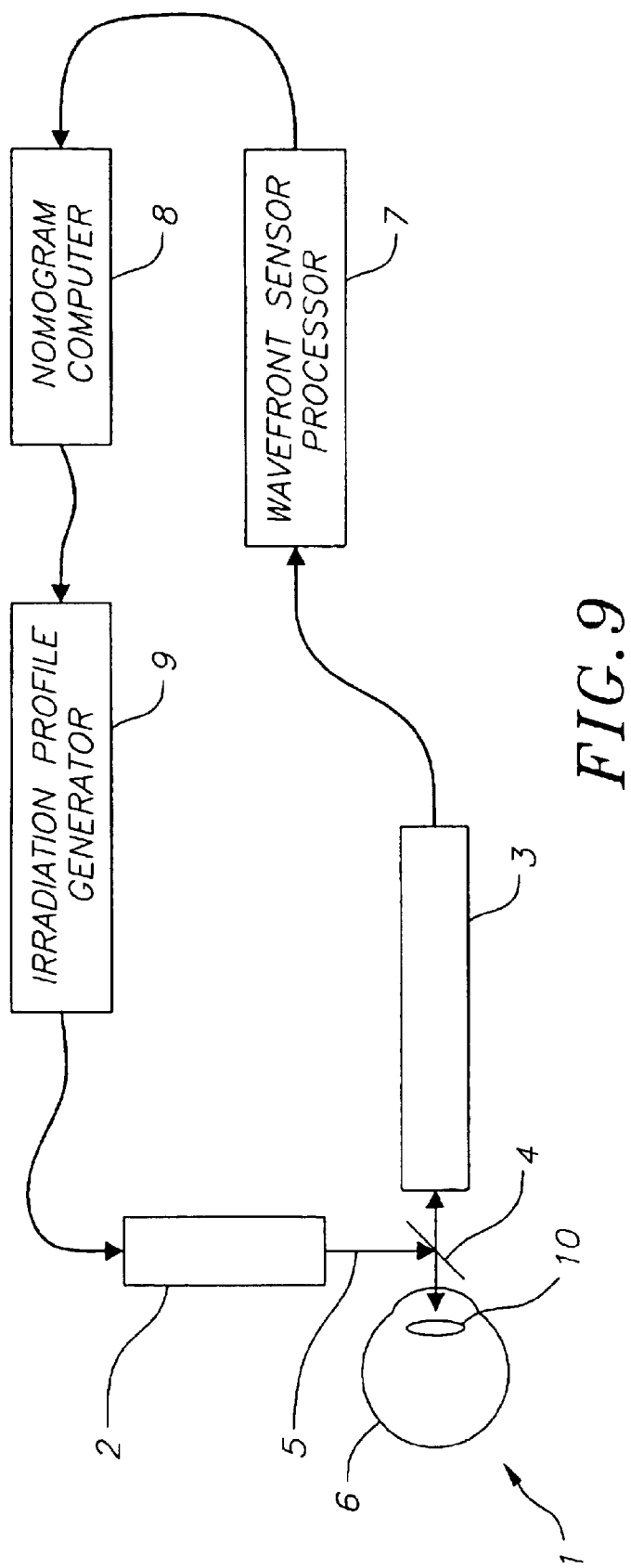
FIG. 9 is a schematic of an apparatus according to the present invention.

In one embodiment, shown schematically in FIG. 9, the apparatus according to the present invention comprises an optical element or optical system (e.g. the eye) 1 having a power adjustable optical element, such as an IOL 10 inserted therein, in optical communication with an irradiation source 2 and a wavefront sensor 3. In the embodiment shown, a beam splitter 4 is placed between the irradiation source 2 and the optical system 1 containing the power adjustable optical element 10 such that an optical path between the optical system 1, the irradiation source 2 and the wavefront sensor 3 is created. In operation, on an optical system such as an eye 1, as shown in FIG. 9, a source of light 5 (from either the light source or the wavefront sensor) passes through the eye 1 where it is focused onto the retina 6. The light 5 is reflected off of the retina 6 and passes back through the eye 1 towards the wavefront sensor 3. The wavefront sensor 3 measures the optical aberrations present in the eye 1. The wavefront sensor 3 measures the magnitude and spatial distribution of the aberrations present in the eye's 1 optical system. This information is fed through a processor 7 into the nomogram computer 8 which, after analysis, determines the correct duration, intensity and spatial distribution of intensities required to correct the measured aberrations. The nomogram computer 8 in turn, communicates with the irradiation profile generator 9 to produce the required light 5 to correct the adjustable optical element (e.g., an IOL) 10 for aberrations detected in the eye 1 in a beam dependent on the physical properties of the optical element 10. In the embodiment shown, the apparatus further comprises a feedback loop, which takes the images and sends those images to a processor 6 in signal communication with the wavefront sensor 3, which analyzes the images and transmits the information to a controller 7, which generates a corrective profile and transmits that corrective profile to an irradiation profile generator 8 in signal communication with the controller 7 and the light source 2. The irradiation profile generator 8 then controls the light source 2 to emit a beam of light 5 which will irradiate the optical element 10 such that the refraction modulating composition RMC dispersed in the polymer matrix of the optical element 10 will be altered to correct the aberration detected in the optical system 1.

The procedure described above may be repeated as many times as necessary, such that after the first dose of irradiation 5, and sufficient time has been allowed for a change in the optical properties of the IOL 10 and eye 1, any remaining aberrations could be detected by the wavefront sensor 3 and another dose of irradiation 5, whose beam characteristics depend on the second aberration measurement, may be applied. This process of aberration measurement, application of a polymerization stimulus, and remeasurement may be continued until the desired optical properties of the eye 1 are achieved or until the IOL 10 is photolocked.

It should be noted that any suitable light source 2, beam splitter 4, wavefront sensor 3, processor 6, controller 7 and irradiation profiler 8 may be used in the current invention such that the optical element aberrations can be analyzed and corrected.

FIGS. 1a to 1d illustrates one inventive embodiment of the current invention in which the refractive index of a particular optical area of the lens 10 is changed by light induced polymerization (thus a change in lens power). The modulated lens power is locked-in via flood irradiation of the entire lens. In the embodiment shown in FIG. 1a, the optical element 10 comprises a FPMC 12 and a RMC 14 dispersed therein. The FPMC 12 forms the optical element framework and is generally responsible for many of its material properties. The RMC 14 may be a single compound or a combination of compounds that is capable of stimulus-induced polymerization, preferably photo-polymerization. As used herein, the term "polymerization" refers to a reaction wherein at least one of the components of the RMC 14 reacts to form at least one covalent or physical bond with either a like component or with a different component. The identities of the FPMC 12 and the RMC 14 will depend on the end use of the optical element 10. However, as a general rule, the FPMC 12 and the RMC 14 are selected such that the components that comprise the RMC 14 are capable of diffusion within the FPMC 12, e.g., a loose FPMC 12 will tend to be paired with larger RMC components 14 and a tight FPMC 12 will tend to be paired with smaller RMC 14.

As shown in FIG. 1b, upon exposure to an appropriate energy source 16 or light), the RMC 14 typically forms a second polymer matrix 18 in the exposed region 20 of the optical element 10. The presence of the second polymer matrix 18 changes the material characteristics of this region 20 of the optical element 10 to modulate its refraction capabilities. In general, the formation of the second polymer matrix 18 typically increases the refractive index of the affected region 20 of the optical element 10.

As shown in FIG. 1c, after exposure, the RMC 14 in the unexposed region 22 will migrate into the exposed region 20 over time. The amount of RMC 14 migration into the exposed region 20 depends upon the frequency, intensity, and duration of the polymerizing stimulus and may be precisely controlled. If enough time is permitted, the RMC 14 will re-equilibrate and redistribute throughout the optical element 10 (i.e., the FPMC 12, including the exposed region). When the region is re-exposed to the energy source 16, the RMC 14 that has since migrated into the region 20 (which may be less than if the RMC 14 were allowed to re-equilibrate) polymerizes to further increase the formation of the second polymer matrix 18. This process (exposure followed by an appropriate time interval to allow for diffusion) may be repeated until the exposed region 20 of the optical element 10 has reached the desired property (e.g., power, refractive index, or shape). The entire optical element 10 is then exposed to the energy source 16 to "lock-in" the desired lens property by polymerizing the remaining RMC 14 that are outside the exposed region 20 before the components 14 can migrate into the exposed region 20, thus forming the final optical element 10, as shown in FIG. 1d. Under these conditions, because freely diffusable RMC 14 are no longer available, subsequent exposure of the optical element 10 to an energy source 16 cannot further change its power.

The FPMC 12 is a covalently or physically linked structure that functions as an optical element 10 and is formed from a FPMC 12. In general, the FPMC 12 comprises one or more monomers that upon polymerization will form the FPMC 12. The FPMC 12 optionally may include any number of formulation auxiliaries that modulate the polymerization reaction or improve any property of the optical element 10. Illustrative examples of suitable FPMC 12 monomers include acrylics, methacrylates, phosphazenes, siloxanes, vinyls, homopolymers, and copolymers thereof. As used herein, a "monomer" refers to any unit (which may itself either be a homopolymer or copolymer) which may be linked together to form a polymer containing repeating units of the same. If the FPMC monomer 12 is a copolymer, it may be comprised of the same type of monomers (e.g., two different siloxanes) or it may be comprised of different types of monomers (e.g., a siloxane and an acrylic).

In one embodiment, the one or more monomers that form the FPMC 12 are polymerized and cross-linked in the presence of the RMC 14. In another embodiment, polymeric starting material that forms the FPMC 12 is cross-linked in the presence of the RMC 14. Under either scenario, the RMC 14 must be compatible with and not appreciably interfere with the formation of the FPMC 12. Similarly, the formation of the second polymer matrix 18 should also be compatible with the existing FPMC 12, such that the FPMC 12 and the second polymer matrix 18 should not phase separate and light transmission by the optical element 10 should be unaffected.

As described previously, the RMC 14 may be a single component or multiple components so long as: (i) it is compatible with the formation of the FPMC 12; (ii) it remains capable of stimulus-induced polymerization after the formation of the FPMC 12; and (iii) it is freely diffusable within the FPMC 12. In one embodiment, the stimulus-induced polymerization is photo-induced polymerization.

The optical elements 10, described herein, have numerous applications in the electronics and data storage industries. The optical elements also have applications in the medical field, such as being used as medical lenses, particularly as IOL. One embodiment of an IOL according to the present invention comprises a FPMC 12 and a RMC 14 dispersed therein. The FPMC 12 and the RMC 14 are as described above with the additional requirement that the resulting lens be biocompatible.

Illustrative examples of a suitable biocompatible FPMC 12 include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("PHPMA"); poly-vinyls such as poly-styrene and poly-N-vinylpyrrolidone ("PNVP"); poly-siloxanes such as poly-dimethylsiloxane; poly-phosphazenes, and copolymers of thereof. U.S. Pat. No. 4,260,725 and patents and references cited therein (which are all incorporated herein by reference) provide more specific examples of suitable polymers that may be used to form the FPMC 12.

In preferred embodiments, the FPMC 12 generally possesses a relatively low glass transition temperature ("$T_g$")

such that the resulting IOL tends to exhibit fluid-like and/or elastomeric behavior, and is typically formed by crosslinking one or more polymeric starting materials wherein each polymeric starting material includes at least one crosslinkable group. Illustrative examples of suitable crosslinkable groups include but are not limited to hydride, acetoxy, alkoxy, amino, anhydride, aryloxy, carboxy, enoxy, epoxy, halide, isocyano, olefinic, and oxime. In more preferred embodiments, each polymeric starting material includes terminal monomers (also referred to as endcaps) that are either the same or different from the one or more monomers that comprise the polymeric starting material but include at least one crosslinkable group, e.g., such that the terminal monomers begin and end the polymeric starting material and include at least one crosslinkable group as part of its structure. Although it is not necessary for the practice of the present invention, the mechanism for crosslinking the polymeric starting material preferably is different than the mechanism for the stimulus-induced polymerization of the components that comprise the RMC 14. For example, if the RMC 14 is polymerized by photo-induced polymerization, then it is preferred that the polymeric starting materials have crosslinkable groups that are polymerized by any mechanism other than photo-induced polymerization.

An especially preferred class of polymeric starting materials for the formation of the FPMC 12 is poly-siloxanes (also known as "silicones") endcapped with a terminal monomer which includes a crosslinkable group selected from the group consisting of acetoxy, amino, alkoxy, halide, hydroxy, and mercapto. Because silicone IOLs tend to be flexible and foldable, generally smaller incisions may be used during the IOL implantation procedure.

An example of an especially preferred polymeric starting material is bis(diacetoxymethylsilyl)-polydimethylsiloxane (which is poly-dimethylsiloxane that is endcapped with a diacetoxymethylsilyl terminal monomer).

The RMC 14 that is used in fabricating IOLs is as described above except that it has the additional requirement of biocompatibility. The RMC 14 is capable of stimulus-induced polymerization and may be a single component or multiple components so long as: (i) it is compatible with the formation of the FPMC 12; (ii) it remains capable of stimulus-induced polymerization after the formation of the FPMC 12; and (iii) it is freely diffusable within the FPMC 12. In general, the same type of monomers that is used to form the FPMC 12 may be used as a component of the RMC 14. However, because of the requirement that the RMC 14 monomers must be diffusable within the FPMC 12, the RMC 14 monomers generally tend to be smaller (i.e., have lower molecular weights) than the monomers which form the FPMC 12. In addition to the one or more monomers, the RMC 14 may include other components such as initiators and sensitizers that facilitate the formation of the second polymer matrix 18.

In preferred embodiments, the stimulus-induced polymerization is photopolymerization. In other words, the one or more monomers that comprise the RMC 14 each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the RMC 14 includes a photoinitiator (any compound used to generate free radicals) either alone or in the presence of a sensitizer. Examples of suitable photoinitiators include acetophenones (e.g., α-substituted haloacetophenones, and diethoxyacetophenone); 2,4-dichloromethyl-1,3,5-triazines; benzoin alkyl ethers; and o-benzoyloximino ketone. Examples of suitable sensitizers include p-(dialkylamino)aryl aldehyde; N-alkylindolylidene; and bis[p-(dialkylamino)benzylidene] ketone.

Because of the preference for flexible and foldable IOLs, an especially preferred class of RMC 14 monomers is poly-siloxanes endcapped with a terminal siloxane moiety that includes a photopolymerizable group. An illustrative representation of such a monomer is:

$$X-Y-X^1$$

wherein Y is a siloxane which may be a monomer, a homopolymer or a copolymer formed from any number of siloxane units, and X and $X^1$ may be the same or different and are each independently a terminal siloxane moiety that includes a photopolymerizable group. An illustrative example of Y include:

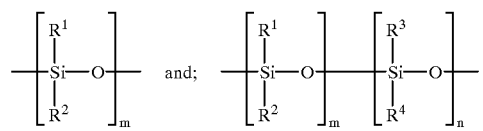

where m and n are independently each an integer and $R^1$, $R^2$, $R^3$, and $R^4$ are independently each hydrogen, alkyl (primary, secondary, tertiary, cyclo), aryl, or heteroaryl. In a preferred embodiment, $R^1$, $R^2$, $R^3$, and $R^4$ are each a $C_1$–$C_{10}$ alkyl or phenyl. Because RMC 14 monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl, or propyl and $R^4$ is phenyl.

Illustrative examples of X and $X^1$ (or $X^1$ and X depending on how the RMC 14 polymer is depicted) are:

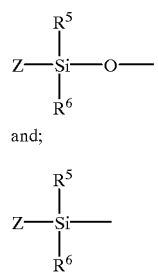

respectively where $R^5$ and $R^6$ are independently each hydrogen, alkyl, aryl, or heteroaryl; and Z is a photopolymerizable group.

In preferred embodiments, $R^5$ and $R^6$ are independently each a $C_1$–$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ are methyl, ethyl, or propyl and Z is a photopolymerizable group that includes an acrylate or methacrylate moiety.

In especially preferred embodiments, an RMC 14 monomer is of the following formula:

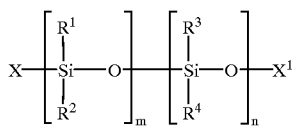

wherein X and X¹ are the same and R¹, R², R³, and R⁴ are as defined previously. Illustrative examples of such RMC 14 monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group.

Although any suitable method may be used, a ring-opening reaction of one or more cyclic siloxanes in the presence of triflic acid has been found to be a particularly efficient method of making one class of inventive RMC 14 monomers. Briefly, the method comprises contacting a cyclic siloxane with a compound of the formula:

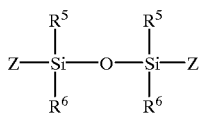

in the presence of triflic acid wherein R⁵, R⁶, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer/tetramer are contacted with bis-methacryloxypropyltetramethyldisiloxane in the presence of triflic acid to form a dimethylsiloxane methylphenylsiloxane copolymer that is endcapped with a methacryloxylpropyldimethylsilane group, an especially preferred RMC 14 monomer.

The IOLs may be fabricated with any suitable method that results in a FPMC 12 with one or more components which comprise the RMC 14 dispersed therein, and wherein the RMC 14 is capable of stimulus-induced polymerization to form a second polymer matrix 18. In general, the method for making an IOL is the same as that for making an optical element 10. In one embodiment, the method comprises mixing a FPMC 12 composition with a RMC 14 to form a reaction mixture; placing the reaction mixture into a mold; polymerizing the FPMC 12 composition to form said optical element 10; and, removing the optical element 10 from the mold.

The type of mold that is used will depend on the optical element being made. For example, if the optical element 10 is a prism, as shown in FIGS. 2a to 2d, then a mold in the shape of a prism is used. Similarly, if the optical element 10 is an IOL, as shown in FIGS. 1a to 1d, then an IOL IOL mold is used and so forth. As described previously, the FPMC 12 composition comprises one or more monomers for forming the FPMC 12 and optionally includes any number of formulation auxiliaries that either modulate the polymerization reaction or improve any property (whether or not related to the optical characteristic) of the optical element 10. Similarly, the RMC 14 comprises one or more components that together are capable of stimulus-induced polymerization to form the second polymer matrix 18. Because flexible and foldable IOLs generally permit smaller incisions, it is preferred that both the FPMC 12 composition and the RMC 14 include one or more silicone-based or low $T_g$ acrylic monomers when the method is used to make IOLs.

Optical properties of the optical element 10 including the IOL as described above can be modified, e.g., by modifying the polymerization of the RMC 14. Such modification can be performed even after implantation of the optical element 10 within the eye. For example, any errors in the power calculation due to imperfect corneal measurements, variable lens positioning, or wound healing may be corrected in a post surgical procedure. In addition, such modification can affect various optical properties, e.g., refractive index and/or radius of curvature. Applicants believe without being bound to any technical limitations that the stimulus-induced polymerization of the RMC forms a second polymer matrix 18 which can change the refractive index and/or the radius of curvature of the IOL in a predictable manner, thus affecting a change in IOL power.

In general, the method for implementing an optical element 10 includes obtaining an optical measurement of the optical element 10 either as a standalone optical element or as an optical element part of a larger optical system, e.g. a light adjustable IOL implanted in the eye, and inducing polymerization of the RMC 14 of the optical element 10 based on the optical measurement. The optical measurement includes measuring aberrations of the optical element 10 or an optical system, e.g., eye comprising the optical element 10. The aberrations measured can be within a lens, an IOL, or an eye with IOL implantation. The aberrations include but are not limited to wavefront or optical aberrations including e.g., defocus, astigmatism, coma, spherical, and higher order optical aberrations. In one embodiment, the optical measurement is obtained after an interval of time, e.g. after an IOLs implantation and wound healing. The optical measurement can be obtained by using any wavefront sensor suitable for detecting aberrations in an optical element, such as, for example a Shack-Hartmann wavefront sensor.

In another embodiment, the optical measurement can be obtained by an adaptive optics system, e.g., a wavefront sensor in combination with a wavefront compensator or modifying element, such as, for example, a deformable mirror, a spatial light phase modulator (SLM), a microelectromechanical membrane, or a segmented micromirror.

Figure 7:
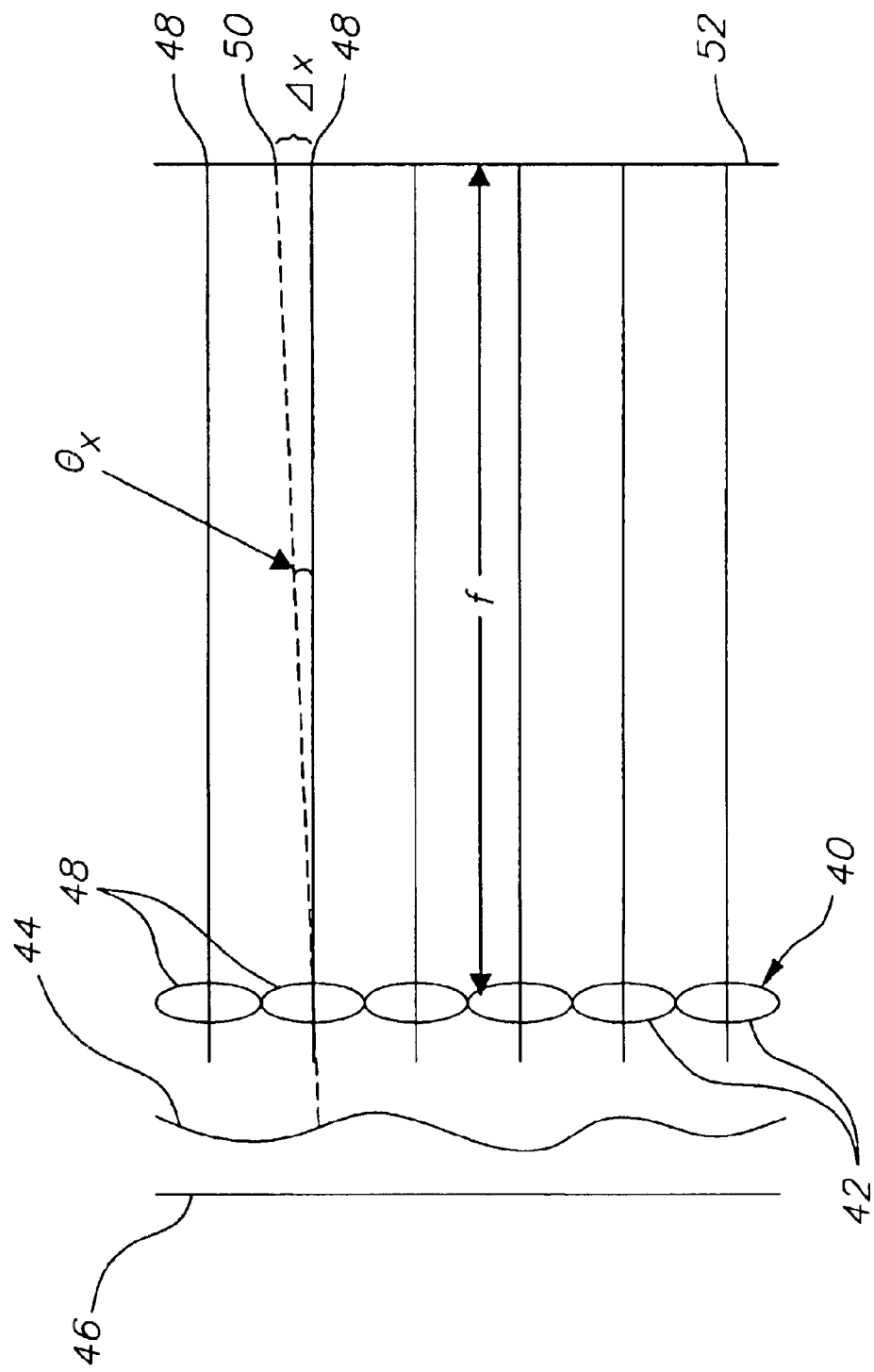
FIG. 7 is a schematic illustrating the Shack-Hartmann wavefront sensor.
Figure 8:
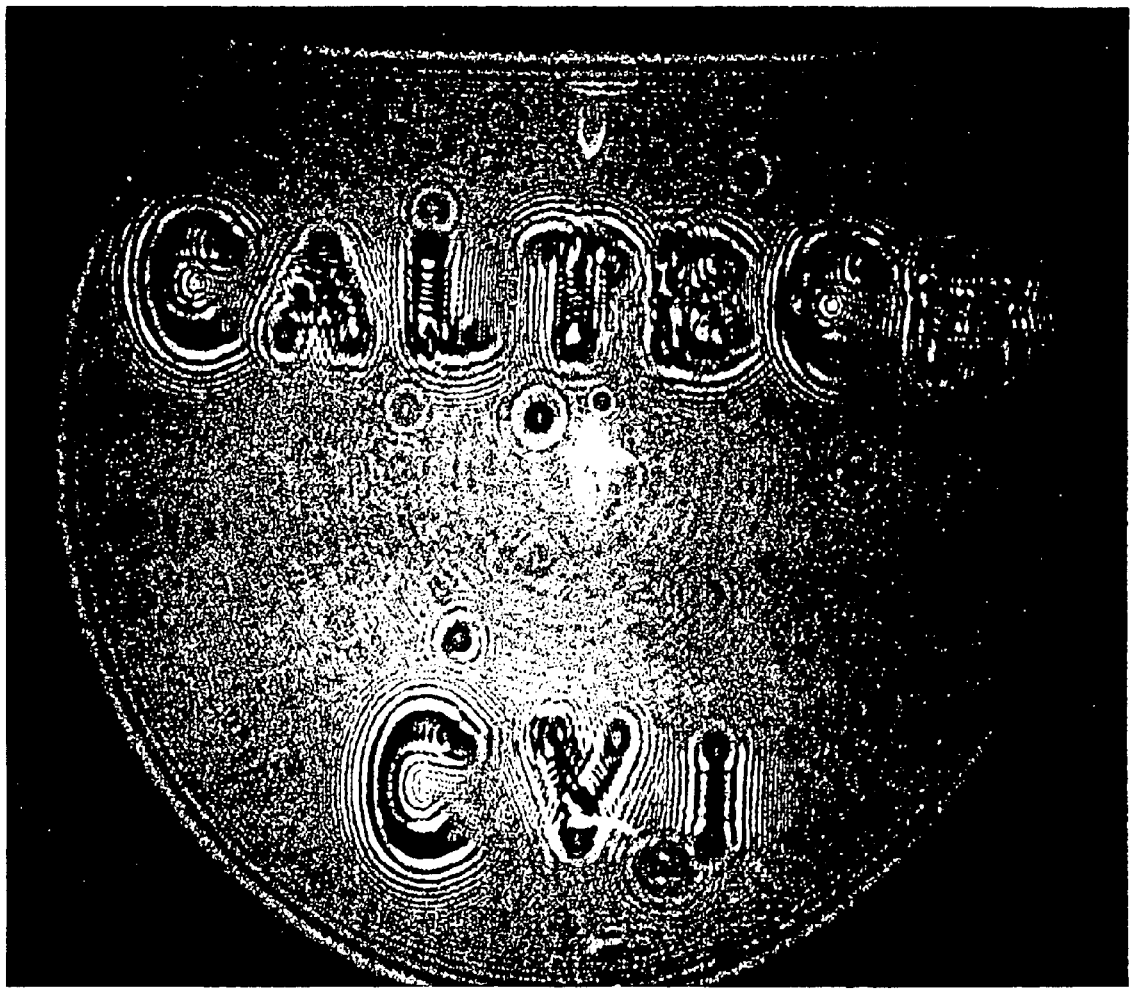
FIG. 8 is the corresponding Ronchi interferogram of a photopolymer film in which "CALTECH" and "CVI" were written using the 325 nm line of He:Cd laser.

The optical measurement can be used to determine the degree and type of modification necessary for obtaining the desired optical properties of an optical element 10 such as an IOL. For example, as shown in FIG. 7, the Shack-Hartmann wavefront sensor detects the aberrations of an optical element 10 or a system comprising the optical element 10; a measurement reflective of these aberrations can be used to determine the extent and spatial distribution of polymerization of the RMC 14 in the optical element 14, e.g., IOL. Polymerization guided by the wavefront analysis, e.g., after IOL implantation corrects aberrations with a fine precision thus maximizing the visual acuity of the eye. In one embodiment, the Shack-Hartmann wavefront sensor is used in combination with a wavefront compensator or modifying element, the Shack-Hartmann sensor detects the aberrations while the wavefront compensator or modifying element corrects the aberrations, e.g., wavefront errors under the control of a closed-loop feedback. Information of the adjustments made by the wavefront compensator or modifying element necessary for correcting the aberrations can be used to determine the extent and distribution of induction in polymerization of the RMC 14.

In another embodiment, the Shack-Hartmann wavefront sensor can be used without the wavefront compensator. The Shack-Hartmann wavefront sensor detects the spatial distribution and magnitude of aberrations present in the optical system, e.g. and eye with a power adjustable IOL. Knowledge of the spatial distribution and magnitude of the aberrations present in the optical element or optical system can be used to determine the necessary spatial intensity distribution and duration of the applied stimulus.

Induction of polymerization of the RMC 14 of an optical element 10 such as an IOL can be achieved by exposing the optical element 10 to a stimulus 16. In general, a method of inducing polymerization of an IOL having a FPMC 12 and a RMC 14 dispersed therein, comprises:

(a) exposing at least a portion of the lens optical element 10 to a stimulus 16 whereby the stimulus 16 induces the polymerization of the RMC 14. If after implantation and wound healing, no IOL property needs to be modified as determined by a wavefront sensor, then the exposed portion is the entire lens. The exposure of the entire lens with intensity sufficient to induce complete polymerization of the RMC throughout the lens will lock in the then-existing properties of the implanted lens.

However, if a lens characteristic such as its optical power needs to be modified, as determined by a wavefront sensor, then the lens must be exposed to the stimulus 16 such that polymerization of the RMC 14 occurs differentially across the lens to compensate for the aberrations detected by the wavefront sensor. Such differential polymerization of the RMC 14 can be achieved via any suitable means of changing the intensity of the stimulus 16 spatially across the lens, such as, for example, by exposing only a portion of the lens to the stimulus 16 via a photomask and collimated beam; or alternatively by utilizing a stimulus source capable of variable intensity across the entire aperture of the lens, such that the lens is subject to a spatially variable stimulus. In one embodiment, the method of implementing the IOL further comprises:

(b) waiting an interval of time; and (c) re-exposing a portion of the lens to the stimulus 16.

This procedure generally will induce the further polymerization of the RMC 14 within the exposed lens region 20. Steps (b) and (c) may be repeated any number of times until the IOL (or optical element) has reached the desired lens characteristic. At this point, the method may further include the step of exposing the entire lens to the stimulus 16 to lock-in the desired lens property.

Induction of the polymerization of the RMC in an IOL can also be achieved by:

(a) exposing a first portion of the lens to a stimulus 16 whereby the stimulus 16 induces the polymerization of the RMC 14; and (b) exposing a second portion of the lens to the stimulus 16.

The first lens portion and the second lens portion represent different regions of the lens although they may overlap. Optionally, the method may include an interval of time between the exposures of the first lens portion and the second lens portion. In addition, the method may further comprise re-exposing the first lens portion and/or the second lens portion any number of times (with or without an interval of time between exposures) or may further comprise exposing additional portions of the lens (e.g., a third lens portion, a fourth lens portion, etc.). Once the desired property has been reached, then the method may further include the step of exposing the entire lens to the stimulus 16 to lock-in the desired lens property.

In general, the location of the one or more exposed portions 20 will vary depending on the type of refractive error being corrected. For example, in one embodiment, the exposed portion 20 of the IOL is the optical zone, which is the center region of the lens (e.g., between about 4 mm and about 5 mm in diameter). Alternatively, the one or more exposed lens portions 20 may be along the IOL's outer rim or along a particular meridian. A stimulus 16 for induction of polymerization of the RMC 14 can be any appropriate coherent or incoherent light source.

In addition, an optical element 10 comprising RMC 14 and a wavefront sensor can be combined to provide an apparatus for correcting aberrations in optical systems, e.g., in eyes. The wavefront sensor can be the Shack-Hartmann wavefront sensor. In one alternative embodiment, the apparatus also includes an optical element comprising RMC 14 in combination with an adaptive optics system comprising a wavefront sensor and a wavefront compensating or modifying device, e.g., a deformable mirror, a spatial light phase modulator (SLM), a micro-electromechanical membrane, or a segmented micromirror.

The following examples are provided for exemplification purposes only and are not intended to limit the scope of the invention which has been described in broad terms above.

EXAMPLE 1

Suitable optical materials comprising various amounts of (a) poly-dimethylsiloxane endcapped with diacetoxymethylsilane ("PDMS") (36000 g/mol), (b) dimethylsiloxane-diphenylsiloxane copolymer endcapped with vinyl-dimethyl silane ("DMDPS") (15,500 g/mol), and (c) a UV-photoinitiator, 2,2-dimethoxy-2-phenylacetophenone ("DMPA") as shown by Table 1 were made and tested. PDMS is the monomer which forms FPMC, and DMDPS and DMPA together comprise the RMC.

TABLE 1

| | PDMS (wt %) | DMDPS (wt %) | DMPA (wt %)[a] |
|---|---|---|---|
| 1 | 90 | 10 | 1.5 |
| 2 | 80 | 20 | 1.5 |
| 3 | 75 | 25 | 1.5 |
| 4 | 70 | 30 | 1.5 |

[a]wt % with respect to DMDPS.

Appropriate amounts of PMDS (Gelest DMS-D33; 36000 g/mol), DMDPS (Gelest PDV-0325; 3.0–3.5 mole % diphenyl, 15,500 g/mol), and DMPA (Acros; 1.5 wt % with respect to DMDPS) were weighed together in an aluminum pan, manually mixed at room temperature until the DMPA dissolved, and degassed under pressure (5 mtorr) for 2–4 minutes to remove air bubbles. Photosensitive prisms, as shown schematically in FIGS. 2a to 2d, were fabricated by pouring the resulting silicone composition into a mold made of three glass slides held together by scotch tape in the form of a prism and sealed at one end with silicone caulk. The prisms are ~5 cm long and the dimensions of the three sides are ~8 mm each. The PDMS in the prisms was moisture cured and stored in the dark at room temperature for a period of 7 days to ensure that the resulting FPMC was non-tacky, clear, and transparent.

The amount of photoinitiator (1.5 wt %) was based on prior experiments with fixed RMC monomer content of 25% in which the photoinitiator content was varied. Maximal refractive index modulation was observed for compositions containing 1.5 wt % and 2 wt % photoinitiator while saturation in refractive index occurred at 5 wt %.

EXAMPLE 2
Synthesis RMC Monomers

As illustrated by Scheme 1, below, commercially available bis-methacryloxylpropyltetramethyl-disiloxane ("MPS") dissociates and then ring-opens the commercially available octamethylcyclotetrasiloxane ("$D_4$") and trimethyltriphenylcyclotrisiloxane ("$D_3$'") in the presence of triflic acid in a one pot synthesis to form linear RMC monomers. U.S. Pat. No. 4,260,725; Kunzler, J. F., Trends in Polymer Science, 4: 52–59 (1996); Kunzler et al. J. Appl. Poly. Sci., 55: 611–619 (1995); and Lai et al., J. Poly. Sci. A. Poly. Chem., 33: 1773–1782 (1995).

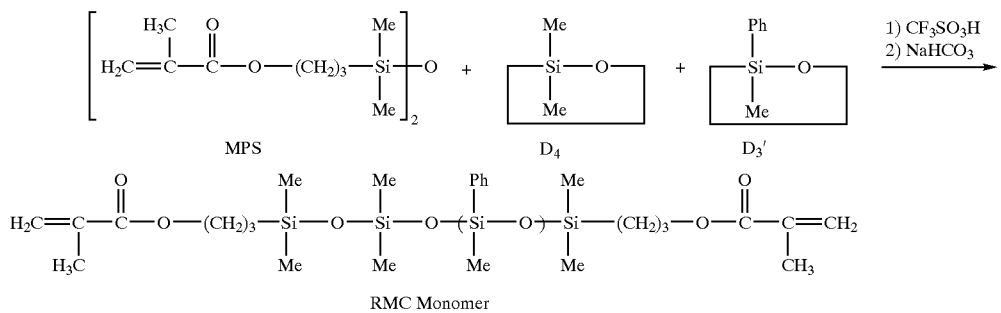

SCHEME 1

RMC Monomer

Appropriate amounts of MPS, $D_4$, and $D_3$' were stirred in a vial for 1.5–2 hours. An appropriate amount of triflic acid was added and the resulting mixture was stirred for another 20 hours at room temperature. The reaction mixture was diluted with hexane, neutralized (the acid) by the addition of sodium bicarbonate, and dried by the addition of anhydrous sodium sulfate. After filtration and rotovaporation of hexane, the RMC monomer was purified by further filtration through an activated carbon column. The RMC monomer was dried at 5 mtorr of pressure between 70–80° C. for 12–18 hours.

The amounts of phenyl, methyl, and endgroup incorporation were calculated from $^1$H-NMR spectra that were run in deuterated chloroform without internal standard tetramethylsilane ("TMS"). Illustrative examples of chemical shifts for some of the synthesized RMC monomers follows. A 1000 g/mole RMC monomer containing 5.58 mole % phenyl (made by reacting: 4.85 g (12.5 mmole) of MPS; 1.68 g (4.1 mmole) of $D_3$'; 5.98 g (20.2 mmole) of $D_4$; and 108 µl (1.21 mmole) of triflic acid: δ=7.56–7.57 ppm (m, 2H) aromatic, δ=7.32–7.33 ppm (m, 3H) aromatic, δ=6.09 ppm (d, 2H) olefinic, δ=5.53 ppm (d, 2H) olefinic, δ=4.07–4.10 ppm (t, 4H) —O—C$\underline{H}_2$CH$_2$CH$_2$—, δ=1.93 ppm (s, 6H) methyl of methacrylate, δ=1.65–1.71 ppm (m, 4H) —O—CH$_2$C$\underline{H}_2$CH$_2$—, δ=0.54–0.58 ppm (m, 4H) —O—CH$_2$CH$_2$C$\underline{H}_2$—Si, δ>0.29–0.30 ppm (d, 3H), C$\underline{H}_3$—Si-Phenyl, δ=0.04–0.08 ppm (s, 50H) (C$\underline{H}_3$)$_2$Si of the backbone.

A 2000 g/mole RMC monomer containing 5.26 mole % phenyl (made by reacting: 2.32 g (6.0 mmole) of MPS; 1.94 g (4.7 mmole) of $D_3$'; 7.74 g (26.1 mmole) of $D_4$; and 136 µl (1.54 mmole) of triflic acid: δ=7.54–7.58 ppm (m, 4H) aromatic, δ=7.32–7.34 ppm (m, 6H) aromatic, δ=6.09 ppm (d, 2H) olefinic, δ=5.53 ppm (d, 2H) olefinic, δ=4.08–4.11 ppm (t, 4H) —O—C$\underline{H}_2$CH$_2$CH$_2$—, δ=1.94 ppm (s, 6H) methyl of methacrylate, δ=1.67–1.71 ppm (m, 4H) —O—CH$_2$C$\underline{H}_2$CH$_2$—, δ=0.54–0.59 ppm (m, 4H) —O—CH$_2$CH$_2$C$\underline{H}_2$—Si, δ=0.29–0.31 ppm (m, 6H), C$\underline{H}_3$—Si-Phenyl, δ=0.04–0.09 ppm (s, 112H) (C$\underline{H}_3$)$_2$Si of the backbone A 4000 g/mole RMC monomer containing 4.16 mole % phenyl (made by reacting: 1.06 g (2.74 mmole) of MPS; 1.67 g (4.1 mmole) of $D_3$'; 9.28 g (31.3 mmole) of $D_4$; and 157 µl (1.77 mmole) of triflic acid: δ=7.57–7.60 ppm (m, 8H) aromatic, δ=7.32–7.34 ppm (m 12H) aromatic, δ=6.10 ppm (d, 2H) olefinic, δ=5.54 ppm (d, 2H) olefinic, δ=4.08–4.12 ppm (t, 4H) —O—C$\underline{H}_2$CH$_2$CH$_2$—, δ=1.94 ppm (s, 6H) methyl of methacrylate, δ=1.65–1.74 ppm (m, 4H) —O—CH$_2$C$\underline{H}_2$CH$_2$—, δ=0.55–0.59 ppm (m, 4H) —O—CH$_2$CH$_2$C$\underline{H}_2$—Si, δ=0.31 ppm (m, 11H), C$\underline{H}_3$—Si-Phenyl, δ=0.07–0.09 ppm (s, 272 H) (C$\underline{H}_3$)$_2$Si of the backbone.

Similarly, to synthesize dimethylsiloxane polymer without any methylphenylsiloxane units and endcapped with methyacryloxypropyldimethylsilane, the ratio of $D_4$ to MPS was varied without incorporating $D'_3$.

Molecular weights were calculated by $^1$H-NMR and by gel permeation chromatography ("GPC"). Absolute molecular weights were obtained by universal calibration method using polystyrene and poly(methyl methacrylate) standards. Table 2 shows the characterization of other RMC monomers synthesized by the triflic acid ring opening polymerization.

TABLE 2

| | Mole % Phenyl | Mole % Methyl | Mole % Methacrylate | Mn (NMR) | Mn (GPC) | $n_D$ |
|---|---|---|---|---|---|---|
| A | 6.17 | 87.5 | 6.32 | 1001 | 946 | 1.44061 |
| B | 3.04 | 90.8 | 6.16 | 985 | 716 | 1.43188 |
| C | 5.26 | 92.1 | 2.62 | 1906 | 1880 | — |
| D | 4.16 | 94.8 | 1.06 | 4054 | 4200 | 1.42427 |
| E | 0 | 94.17 | 5.83 | 987 | 1020 | 1.42272 |
| F | 0 | 98.88 | 1.12 | 3661 | 4300 | 1.40843 |

At 10–40 wt %, these RMC monomers of molecular weights 1000 to 4000 g/mol with 3–6.2 mole % phenyl content are completely miscible, biocompatible, and form optically clear prisms and lenses when incorporated in the silicone matrix. RMC monomers with high phenyl content (4–6 mole %) and low molecular weight (1000–4000 g/mol) resulted in increases in refractive index change of 2.5 times and increases in speeds of diffusion of 3.5 to 5.0 times compared to the RMC monomer used in Table 1 (dimethylsiloxane-diphenylsiloxane copolymer endcapped with vinyldimethyl silane ("DMDPS") (3–3.5 mole % diphenyl content, 15500 g/mol). These RMC monomers were used to make optical elements comprising: (a) polydimethylsiloxane endcapped with diacetoxymethylsilane ("PDMS") (36000 g/mol), (b) dimethylsiloxane methylphenylsiloxane copolymer that is endcapped with a methacryloxypropyldimethylsilane group, and (c) 2,2-dimethoxy-2- phenylacetophenone ("DMPA"). Note that component (a) is the monomer that forms the FPMC and components (b) and (c) comprise the RMC.

EXAMPLE 3

Fabrication of Intraocular Lenses ("IOL")

An IOL mold was designed according to well-accepted standards. See e.g., U.S. Pat. Nos. 5,762,836; 5,141,678; and 5,213,825. Briefly, the mold is built around two plano-concave surfaces possessing radii of curvatures of −6.46 mm and/or −12.92 mm, respectively. The resulting lenses are 6.35 mm in diameter and possess a thickness ranging from 0.64 mm, 0.98 mm, or 1.32 mm depending upon the combination of concave lens surfaces used. Using two different radii of curvatures in their three possible combinations and assuming a nominal refractive index of 1.404, but not limited to, for the IOL composition, lenses with pre-irradiation powers of 10.51 D (62.09 D in air), 15.75 D (92.44 in air), and 20.95 D (121.46 D in air) were fabricated.

EXAMPLE 4

Stability of Compositions Against Leaching

Three IOLs were fabricated with 30 and 10 wt % of RMC monomers B and D incorporated in 60 wt % of the PDMS matrix. After moisture curing of PDMS to form the FPMC, the presence of any free RMC monomer in the aqueous solution was analyzed as follows. Two out of three lenses were irradiated three times for a period of 2 minutes using 340 nm light, while the third was not irradiated at all. One of the irradiated lenses was then locked by exposing the entire lens matrix to radiation. All three lenses were mechanically shaken for 3 days in 1.0 M NaCl solution. The NaCl solutions were then extracted by hexane and analyzed by $^1$H-NMR. No peaks due to the RMC monomer were observed in the NMR spectrum. These results suggest that the RMC monomers did not leach out of the matrix into the aqueous phase in all three cases. Earlier studies on a vinyl endcapped silicone RMC monomer showed similar results even after being stored in 1.0 M NaCl solution for more than one year.

Matrix assisted laser desorption ionization time of flight (MALDI-TOF) mass spectrometry was employed to further study the potential leaching of monomer and matrix into aqueous solutions. Four lenses were examined in this study. The first lens was fabricated with 30 and 10 wt % monomers E and F incorporated in 60 wt % of the PDMS matrix. This lens was exposed to 2.14 mW/cm$^2$ of 325 nm light from a He:Cd laser for four minutes after placing a 0.5 mm width astigmatism mask 23° clockwise from vertical over the lens. The first lens was then photolocked three hours after the initial irradiation by exposure to a low pressure Hg lamp for 8 minutes. The second lens was composed of 30 and 10 wt % monomers B and D incorporated in 60 wt % of the PDMS matrix. This lens was exposed to 3.43 mW/cm$^2$ of 340 nm light from a Xe:Hg arc lamp after placing a 1 mm diameter photomask over the central portion of the lens. The second lens was not photolocked. The third lens was fabricated with 30 and 10 wt % monomers E and F incorporated in 60 wt % of the PDMS matrix. This lens was exposed to 2.14 mW/cm$^2$ of 325 nm light from a He:Cd laser for four minutes after placing a 1.0 mm diameter photomask over the central portion of the lens. The third lens was then photolocked three hours after the initial irradiation by exposure to a low pressure Hg lamp for 8 minutes. The fourth lens was fabricated with 30 and 10 wt % monomers E and F incorporated in 60 wt % of the PDMS matrix. The fourth lens was not irradiated. The four lenses were placed individually into 5 ml of doubly distilled water. One ml of dish washing detergent (a surfactant) was added to the solution containing lens #2. The lenses were kept in their respective solutions for 83 days at room temperature. After this time, the lenses, in their respective solutions, were placed into an oven maintained at 37° C. for 78 days. Each of the aqueous solutions were then extracted three times using approximately 5 ml of hexane. All hexane extracts from each lens solution were combined, dried over anhydrous sodium sulfate (Na$_2$SO$_4$), and allowed to evaporate to dryness. Each of the four vials was then extracted with THF, spotted onto a dihydroxy benzoic acid matrix, and analyzed by MALDI-TOF. For comparison, each of the monomers and PDMS matrix were run in their pure form. Comparison of the four extracted lens samples and the pure components showed no presence of any of the monomers or matrix indicating that monomer and matrix were not leaching out of the lenses.

EXAMPLE 5

Toxicological Studies in Rabbit Eyes

Sterilized, unirradiated, and irradiated silicone IOLs (fabricated as described in Example 3) of the present invention and a sterilized commercially available silicone IOL were implanted in albino rabbit eyes. After clinically following the eyes for one week, the rabbits were sacrificed. The extracted eyes were enucleated, placed in formalin and studied histopathologically. There is no evidence of corneal toxicity, anterior segment inflammation, or other signs of lens toxicity.

EXAMPLE 6

Irradiation of Silicone Prisms

Because of the ease of measuring refractive index change (Δn) and percent net refractive index change (% Δn) of prisms, the inventive formulations were molded into prisms 26 for irradiation and characterization, as shown in FIGS. 2a to 2d. As shown in FIG. 2a, the prisms 26 were fabricated by mixing and pouring (a) 90–60 wt % of high M$_n$ PDMS 12 (FPMC), (b) 10–40 wt % of RMC 14 monomers in Table 2, and (c) 0.75 wt % (with respect to the RMC monomers) of the photoinitiator DMPA into glass molds in the form of prisms 5.0 cm long and 8.0 mm on each side. The silicone composition in the prisms 26 was moisture cured and stored in the dark at room temperature for a period of 7 days to ensure that the final matrix was non-tacky, clear, and transparent.

FIGS. 2a to 2d illustrate the prism irradiation procedure. Two of the long sides of each prisms 26 were covered by a black background while the third was covered by a photomask 28 made of an aluminum plate 30 with rectangular windows 32 (2.5 mm×10 mm), as shown in FIG. 2b. Each 26 was exposed to 3.4 mW/cm$^2$ of collimated 340 nm light 16 (peak absorption of the photoinitiator) from a 1000 W Xe:Hg arc lamp for various time periods.

The prisms 26 with the photomask 28 were subject to both (i) continuous irradiation—one-time exposure for a known time period, and (ii) "staccato" irradiation—three shorter exposures with long intervals between them. During continuous irradiation, the refractive index contrast is dependent on the crosslinking density and the mole % phenyl groups, while in the interrupted irradiation; RMC 14 monomer diffusion and further crosslinking also play an important role. During staccato irradiation, the RMC 14 monomer polymerization depends on the rate of propagation during each exposure and the extent of interdiffusion of free RMC 14 monomer during the intervals between exposures. Typical values for the diffusion coefficient of oligomers (similar to the 1000 g/mole RMC 14 monomers used in the practice of the present invention) in a silicone matrix are on the order of $10^{-6}$ to $10^{-7}$ cm²/s. In other words, the inventive RMC 14 monomers require approximately 2.8 to 28 hours to diffuse 1 mm (roughly the half width of the irradiated bands). The distance of a typical optical zone in an IOL is about 4 to about 5 mm across. However, the distance of the optical zone may also be outside of this range. After the appropriate exposures, the prisms 26 were irradiated without the photomask (thus exposing the entire matrix) for 6 minutes using a medium pressure mercury-arc lamp, as shown in FIG. 2*d*. This polymerized the remaining silicone RMC 14 monomers and thus "locked" the refractive index of the prism in place.

EXAMPLE 7
Prism Dose Response Curves

Inventive prisms 26 fabricated from RMC 14 monomers described by Table 2 were masked and initially exposed for 0.5, 1, 2, 5, and 10 minutes using 3.4 mW/cm² of the 340 nm line from a 1000 W Xe:Hg arc lamp, as shown schematically in FIGS. 2*a* to 2*d*. The exposed regions 20 of the prisms 26 were marked, the mask 28 detached and the refractive index changes measured. The refractive index modulation of the prisms 26 was measured by observing the deflection of a sheet of laser light passed through the prism 26. The difference in deflection of the beam passing through the exposed 20 and unexposed 22 regions was used to quantify the refractive index change ($\Delta n$) and the percentage change in the refractive index (% $\Delta n$).

After three hours, the prisms 26 were remasked with the windows 32 overlapping with the previously exposed regions 20 and irradiated a second time for 0.5, 1, 2, and 5 minutes (total time thus equaled 1, 2, 4, and 10 minutes respectively). The masks 28 were detached and the refractive index changes measured. After another three hours, the prisms were exposed a third time for 0.5, 1, and 2 minutes (total time thus equaled 1.5, 3, and 6minutes) and the refractive index changes were measured. As expected, the % $\Delta n$ increased with exposure time for each prism 26 after each exposure resulting in prototypical dose response curves. Based upon these results, adequate RMC 14 monomer diffusion appears to occur in about 3 hours for 1000 g/mole RMC 14 monomer.

All of the RMC monomers (B–F) except for RMC monomer A resulted in optically clear and transparent prisms before and after their respective exposures. For example, the largest % $\Delta n$ for RMC monomers B, C, and D at 40 wt % incorporation into 60 wt % FPMC were 0.52%, 0.63% and 0.30% respectively which corresponded to 6 minutes of total exposure (three exposures of 2 minutes each separated by 3 hour intervals for RMC monomer B and 3 days for RMC monomers C and D). However, although it produced the largest change in refractive index (0.95%), the prism fabricated from RMC monomer A (also at 40 wt % incorporation into 60 wt % FPMC and 6 minutes of total exposure—three exposures of 2 minutes each separated by 3 hour intervals) turned somewhat cloudy. Thus, if RMC monomer A were used to fabricate an IOL, then the RMC must include less than 40 wt % of RMC monomer A or the % $\Delta n$ must be kept below the point where the optical clarity of the material is compromised.

A comparison between the continuous and staccato irradiation for RMC A and C in the prisms shows that lower % $\Delta n$ values occurs in prisms exposed to continuous irradiation as compared to those observed using staccato irradiations. As indicated by these results, the time interval between exposures (which is related to the amount of RMC diffusion from the unexposed to exposed regions) may be exploited to precisely modulate the refractive index of any material made from the inventive polymer compositions.

Exposure of the entire, previously irradiated prisms to a medium pressure Hg arc lamp polymerized any remaining free RMC, effectively locking the refractive index contrast. Measurement of the refractive index change before and after photolocking indicated no further modulation in the refractive index.

EXAMPLE 8
Optical Characterization of IOLs

Figure 3A:
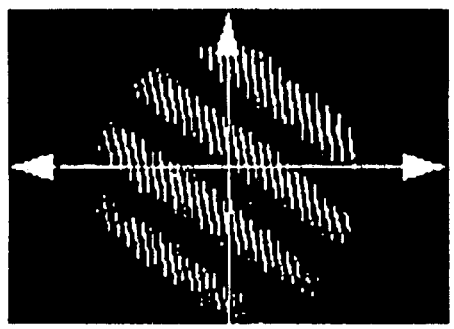
FIG. 3a shows unfiltered Moire fringe patterns of an inventive IOL. The angle between the two Ronchi rulings was set at 12° and the displacement distance between the first and second Moiré patterns was 4.92 mm.
Figure 3B:
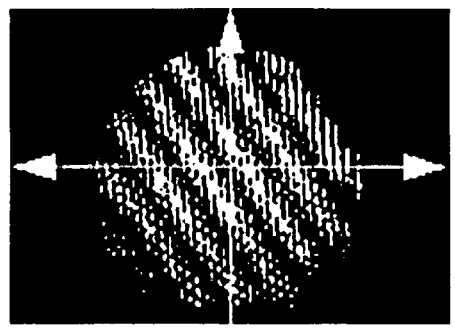
FIG. 3b shows unfiltered Moiré fringe patterns of an inventive IOL. The angle between the two Ronchi rulings was set at 12° and the displacement distance between the first and second Moiré patterns was 4.92 mm.
Figure 4:
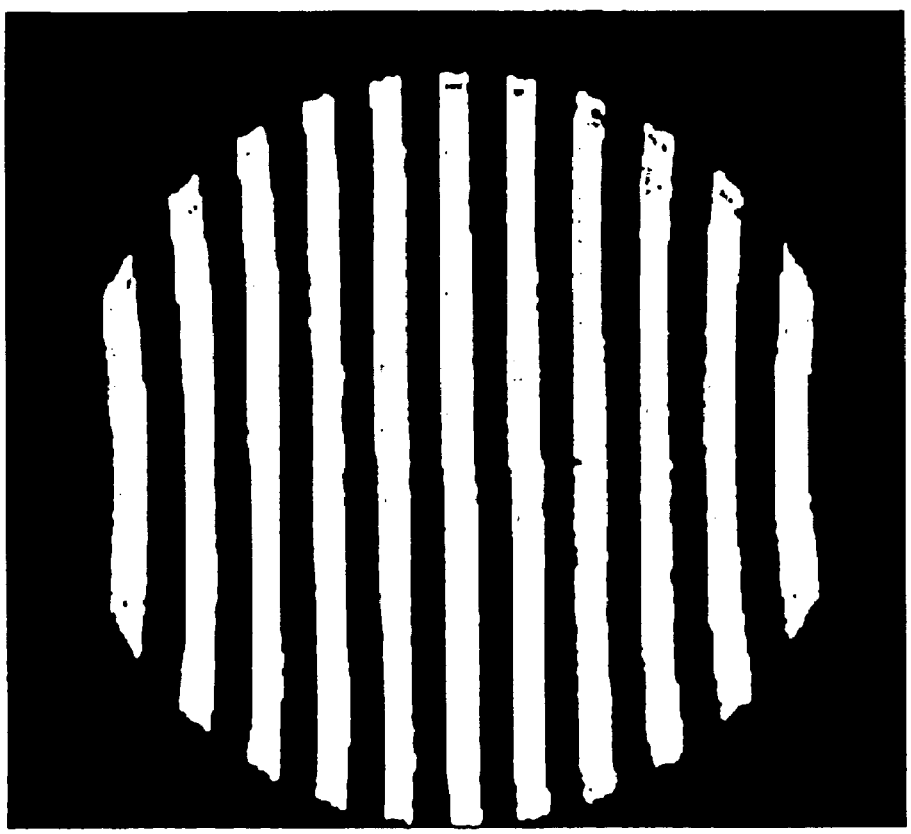
FIG. 4 is a Ronchigram of an inventive IOL. The Ronchi pattern corresponds to a 2.6 mm central region of the lens.

Talbot interferometry and the Ronchi test, as shown in FIGS. 3*a*, 3*b* and 4 were used to qualitatively and quantitatively measure any primary optical aberrations (primary spherical, coma, astigmatism, field curvature, and distortion) present in pre- and post-irradiated lenses as well as quantifying changes in power upon photopolymerization.

In Talbot interferometry, the test IOL is positioned between the two Ronchi rulings with the second grating placed outside the focus of the IOL and rotated at a known angle, θ, with respect to the first grating. Superposition of the autoimage of the first Ronchi ruling ($p_1$=300 lines/inch) onto the second grating ($P_2$=150 lines/inch) produces Moiré fringes inclined at an angle, $\alpha_1$. A second Moiré fringe pattern is constructed by axial displacement of the second Ronchi ruling along the optic axis a known distance, d, from the test lens. Displacement of the second grating allows the autoimage of the first Ronchi ruling to increase in magnification causing the observed Moiré fringe pattern to rotate to a new angle, $\theta_2$. Knowledge of Moiré pitch angles permits determination of the focal length of the lens (or inversely its power) through the expression:

$$f = \frac{p_1}{p_2} d \left( \frac{1}{\tan\alpha_2 \sin\theta + \cos\theta} - \frac{1}{\tan\alpha_1 \sin\theta + \cos\theta} \right)^{-1} \quad (1)$$

To illustrate the applicability of Talbot interferometry to this work, Moiré fringe patterns of one of the inventive, pre-irradiated IOLs (60 wt % PDMS, 30 wt % RMC monomer B, 10 wt % RMC monomer D, and 0.75% DMPA relative to the two RMC monomers) measured in air is presented in FIGS. 3*a* and 3*b*. Each of the Moiré fringes was fitted with a least squares fitting algorithm specifically designed for the processing of Moiré patterns. The angle between the two Ronchi rulings was set at 12°, the displacement between the second Ronchi ruling between the first and second Moiré fringe patterns was 4.92 mm, and the pitch angles of the Moiré fringes, measured relative to an orthogonal coordinate system defined by the optic axis of the instrument and crossing the two Ronchi rulings at 90°, were $\alpha_1$=−33.2°±0.30° and $\alpha_2$=−52.7°±0.40°. Substitution of these values into the above equation results in a focal length of 10.71±0.50 mm (power=93.77±4.6 D).

Optical aberrations of the inventive IOLs (from either fabrication or from the stimulus-induced polymerization of the RMC components) were monitored using the "Ronchi Test" which involves removing the second Ronchi ruling from the Talbot interferometer and observing the magnified autoimage of the first Ronchi ruling after passage though the test IOL. The aberrations of the test lens manifest themselves by the geometric distortion of the fringe system (produced by the Ronchi ruling) when viewed in the image plane. Knowledge of the distorted image reveals the aberration of the lens. In general, the inventive fabricated lenses (both pre and post irradiation treatments) exhibited sharp, parallel, periodic spacing of the interference fringes indicating an absence of the majority of primary-order optical aberrations, high optical surface quality, homogeneity of n in the bulk, and constant lens power. FIG. 4 is an illustrative example of a Ronchigram of an inventive, pre-irradiated IOL that was fabricated from 60 wt % PDMS, 30 wt % RMC monomer B, 10 wt % RMC monomer D, and 0.75% of DMPA relative to the 2 RMC monomers.

The use of a single Ronchi ruling may also be used to measure the degree of convergence of a refracted wavefront (i.e., the power). In this measurement, the test IOL is placed in contact with the first Ronchi ruling, collimated light is brought incident upon the Ronchi ruling, and the lens and the magnified autoimage is projected onto an observation screen. Magnification of the autoimage enables measurement of the curvature of the refracted wavefront by measuring the spatial frequency of the projected fringe pattern. These statements are quantified by the following equation:

$$P_v = \frac{1000}{L}\left(1 + \frac{d_s}{d}\right) \quad (2)$$

wherein $P_v$ is the power of the lens expressed in diopters, L is the distance from the lens to the observing plane, $d_s$, is the magnified fringe spacing of the first Ronchi ruling, and d is the original grating spacing.

EXAMPLE 9
Power Changes from Photopolymerization of the Inventive IOLs

An inventive IOL 10 was fabricated as described by Example 3 comprising 60 wt % PDMS 12 ($n_D$=1.404), 30 wt % of RMC monomer B 14 ($n_D$=1.4319), 10 wt % of RMC monomer D 14 ($n_D$=1.4243), and 0.75 wt % of the photoinitiator DMPA relative to the combined weight percents of the two RMC 14 monomers. The IOL 10 was fitted with a 1 mm diameter photomask 28 and exposed to 3.4 mW/cm² of 340 nm collimated light 16 from a 1000 W Xe:Hg arc lamp for two minutes, as shown in FIG. 5a. The irradiated lens 10 was then placed in the dark for three hours to permit polymerization and RMC 14 monomer diffusion, as shown in FIG. 5b. The IOL 10 was photolocked by continuously exposing the entire lens 10 for six minutes using the aforementioned light conditions, as shown in FIG. 5c. Measurement of the Moiré pitch angles followed by substitution into equation 1 resulted in a power of 95.1±2.9 D (f=10.52±0.32 mm) and 104.1±3.6 D (f=9.61 mm±0.32 mm) for the unirradiated 22 and irradiated 20 zones, respectively.

The magnitude of the power increase was more than what was predicted from the prism experiments where a 0.6% increase in the refractive index was routinely achieved. If a similar increase in the refractive index was achieved in the IOL, then the expected change in the refractive index would be 1.4144 to 1.4229. Using the new refractive index (1.4229) in the calculation of the lens power (in air) and assuming the dimensions of the lens did not change upon photopolymerization, a lens power of 96.71 D (f=10.34 mm) was calculated. Since this value is less than the observed power of 104.1±3.6 D, the additional increase in power must be from another mechanism.

Further study of the photopolymerized IOL 10 showed that subsequent RMC 14 monomer diffusion after the initial radiation exposure leads to changes in the radius of curvature of the lens 10, as shown in FIG. 5d. The RMC 14 monomer migration from the unirradiated zone 22 into the irradiated zone 20 causes either or both of the anterior 34 and posterior 36 surfaces of the lens 10 to swell thus changing the radius of curvature of the lens 10. It has been determined that a 7% decrease in the radius of curvature for both surfaces 34 and 36 is sufficient to explain the observed increase in lens power.

Figure 6A:
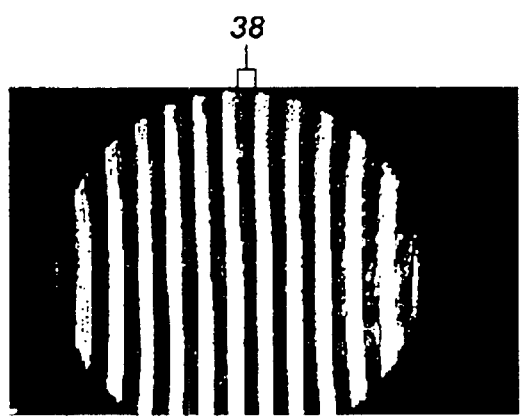
FIG. 6a are Ronchi interferograms of an IOL before and after laser treatment depicting approximately a +8.6 diopter change in lens power within the eye. The spacing of alternative light and dark bands is proportional to lens power.
Figure 6B:
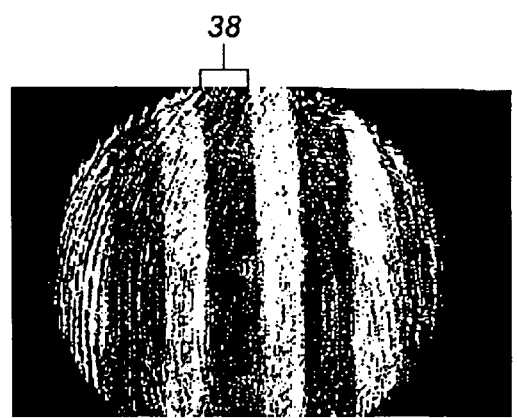
FIG. 6b are Ronchi interferograms of an IOL before and after laser treatment depicting approximately a +8.6 diopter change in lens power within the eye. The spacing of alternative light and dark bands is proportional to lens power.

The concomitant change in the radius of curvature was further studied. An identical IOL 10 described above was fabricated. A Ronchi interferogram of the IOL 10 is shown in FIG. 6a (left interferogram). Using a Talbot interferometer, the focal length of the lens 10 was experimentally determined to be 10.52±0.30 mm (95.1 D±2.8 D). The IOL 10 was then fitted with a 1 mm photomask 28 and irradiated with 1.2 mW of 340 collimated light 16 from a 1000 W Xe:Hg arc lamp continuously for 2.5 minutes. Unlike the previous IOL, this lens 10 was not "locked in" three hours after irradiation. FIG. 6b (right interferogram) is the Ronchi interferogram of the lens 10 taken six days after irradiation. The most obvious feature between the two interference patterns is the dramatic increase in the fringe spacing 38, which is indicative of an increase in the refractive power of the lens 10.

Measurement of the fringe spacings 38 indicates an increase of approximately +38 diopters in air (f≈7.5 mm). This corresponds to a change in the order of approximately +8.6 diopters in the eye. Since most post-operative corrections from cataract surgery are within ±2 D, this experiment indicates that the use of the inventive IOLs will permit a relatively large therapeutic window.

EXAMPLE 10
Photopolymerization Studies of Non-Phenyl-Containing IOLs

Inventive IOLs 10 using non-phenyl containing RMC monomers 14 were fabricated to further study the swelling from the formation of the second polymer matrix 18. An illustrative example of such an IOL 10 was fabricated from 60 wt % PDMS, 30 wt % RMC monomer E, 10 wt % RMC monomer F, and 0.75% DMPA relative to the two RMC monomers. The pre-irradiation focal length of the resulting IOL was 10.76 mm±0.25 mm (92.94±2.21 D).

In this experiment, the light source 16 was a 325 nm laser line from a He:Cd laser. A 1 mm diameter photomask 28 was placed over the lens 10 and exposed to a collimated flux 16 of 2.14 mW/cm² at 325 nm for a period of two minutes. The lens 10 was then placed in the dark for three hours. Experimental measurements indicated that the focal length of the IOL 10 changed from 10.76 mm±0.25 mm (92.94 D±2.21 D) to 8.07 mm±0.74 mm (123.92 D±10.59 D) or a dioptric change of +30.98D±10.82 D in air. This corresponds to an approximate change of +6.68 D in the eye. The amount of irradiation required to induce these changes is only 0.257 J/cm².

EXAMPLE 11
Monitoring for Potential IOL Changes from Ambient Light

The optical power and quality of the inventive IOLs were monitored to show that handling under ambient light conditions does not produce any unwanted changes in lens power. A 1 mm open diameter photomask was placed over the central region of an inventive IOL (containing 60 wt % PDMS, 30 wt % RMC monomer E, 10 wt % RMC monomer F, and 0.75 wt % DMPA relative to the two RMC monomers), exposed to continuous room light for a period of 96 hours, and the spatial frequency of the Ronchi patterns as well as the Moiré fringe angles were monitored every 24 hours. Using the method of Moiré fringes, the focal length measured in the air of the lens immediately after removal from the lens mold is 10.87±0.23 mm (92.00 D±1.98 D) and after 96 hours of exposure to ambient room light is 10.74 mm±0.25 mm (93.11 D±2.22 D). Thus, within the experimental uncertainty of the measurement, it is shown that ambient light does not induce any unwanted change in power. A comparison of the resulting Ronchi patterns showed no change in spatial frequency or quality of the interference pattern, confirming that exposure to room light does not affect the power or quality of the inventive IOLs.

EXAMPLE 12
Effect of the Lock in Procedure of an Irradiated IOL

An inventive IOL whose power had been modulated by irradiation was tested to see if the lock-in procedure resulted in further modification of lens power. An IOL fabricated from 60 wt % PDMS, 30 wt % RMC monomer E, 10 wt % RMC monomer F, and 0.75% DMPA relative to the two RMC monomers was irradiated for two minutes with 2.14 mW/cm$^2$ of the 325 nm laser line from a He:Cd laser and was exposed for eight minutes to a medium pressure Hg arc lamp. Comparisons of the Talbot images before and after the lock in procedure showed that the lens power remained unchanged. The sharp contrast of the interference fringes indicated that the optical quality of the inventive lens also remained unaffected.

To determine if the lock-procedure was complete, the IOL was refitted with a 1 mm diameter photomask and exposed a second time to 2.14 mW/cm$^2$ of the 325 nm laser line for two minutes. As before, no observable change in fringe space or in optical quality of the lens was observed.

EXAMPLE 13
Monitoring for Potential IOL Changes from the Lock-In

A situation may arise wherein the implanted IOL does not require post-operative power modification. In such cases, the IOL must be locked in so that its characteristic will not be subject to change. To determine if the lock-in procedure induces undesired changes in the refractive power of a previously unirradiated IOL, the inventive IOL (containing 60 wt % PDMS, 30 wt % RMC monomer E, 10 wt % RMC monomer F, and 0.75 wt % DMPA relative to the two RMC monomers) was subject to three 2 minute irradiations over its entire area that was separated by a 3 hour interval using 2.14 mW/cm$^2$ of the 325 nm laser line from a He:Cd laser. Ronchigrams and Moiré fringe patterns were taken prior to and after each subsequent irradiation. The Moiré fringe patterns taken of the inventive IOL in air immediately after removal from the lens mold and after the third 2 minute irradiation indicate a focal length of 10.50 mm±0.39 mm (95.24 D±3.69 D) and 10.12 mm±10.39 mm (93.28 D±3.53D) respectively. These measurements indicate that photolocking a previously unexposed lens does not induce unwanted changes in power. In addition, no discernable change in fringe spacing or quality of the Ronchi fringes was detected indicating that the refractive power had not changed due to the lock-in.

EXAMPLE 14
Application of a Wavefront Sensor to an IOL Capable of Post-Implantation Power Modification
a. Shack-Hartmann Wavefront Sensor The basic theory of a Shack-Hartmann wavefront sensor used to measure the aberrations of an optical system is based upon the concept that a portion (i.e. a subaperture) of a converging wavefront tilted relative to an ideal wavefront causes light to come to a focus at a place other than the intended focus. The converse can be used to determine the tilt error in a portion of the wavefront by determining where the light from that region intercepts some plane, and the corresponding difference between that intersection and the one expected from a perfect/ideal wavefront.

The Shack-Hartmann wavefront sensor uses a lens array to measure the localized slopes of an aberrated wavefront. As shown in FIG. 7, the sensor 40 is constructed from an array of spherical lenses or two identical layers of cylindrical lenses arranged at 90° with respect to each other forming a two-dimensional array of spherical lenslets 42. These lenslets 42 divide the wavefront 44 under test into a number of sub apertures, which bring the light to an array of foci in the focal plane of the lens array 42. The test of an ideal, wave 46 results in a regular array of focus spots 48, each spot being located on the optical-axis of the corresponding lenslet 42. If an aberrated wavefront 44 is used, the image spot 50 on an image plane 52 at each sub-aperture shifts with respect to the corresponding point 48 in the reference pattern by a factor proportional to the local tilt. The local slopes, or the partial derivatives, of the tested wavefront 44 can therefore be detected by measurement of the shift of these focus spots 48 and 50. FIG. 7 depicts how the tilt at each passage through a lenslet 42 is established. The solid and dashed lines represent the wave normals to the ideal 46 and aberrated 44 converging wavefronts, respectively, after ideal 46 and aberrated 44 converging wavefronts, respectively, after passage through the array of lenslets 42. From the figure, Δx is the value of one of the components of beam deviation, f is the focal length of the lenslet array, and $\theta_x$ is the angular tilt of the aberrated wavefront 44 from ideality. The partial derivatives of the tested wavefront 44 W (x,y) at the sampling positions (x,y) are obtained from the relationships $$\frac{\partial W(x, y)}{\partial x} = \frac{\Delta x}{f} \tag{3a}$$

$$\frac{\partial W(x, y)}{\partial y} = \frac{\Delta y}{f} \tag{3b}$$

b. Application of a Shack-Hartmann Wavefront Sensor and Wavefront Compensator to Correct for the Optical Aberrations of the Human Eye The Shack-Hartmann wavefront sensor can be used in a human eye and optionally in conjunction with a wavefront compensator. In particular, an optical measurement can be obtained by first establishing a set of reference spots from an ideal wavefront. In the absence of the eye, a well collimated beam is directed through an optical system and passed through the Shack-Hartmann wavefront sensor where it is focused onto the viewing screen. Using this pattern as a reference removes any phase errors or aberrations inherent to the optical system. A compact source of incoherent or coherent light is then focused onto the retina. If the eye possesses aberrations, the light reflected from the retina forms a distorted wavefront as it exits the eye. The pupil of the distorted wavefront is then focused onto the surface of the deformable mirror (or appropriate wavefront compensating device) initially kept flat (or in the off position) and then transmitted to the Shack-Hartmann wavefront sensor. The deformable mirror or appropriate wavefront compensating device lies in a plane conjugate to both the eye's pupil plane and the lenslet array of the wavefront sensor. The two-dimensional lenslet array samples the wavefront and forms an array of focused spots onto a photographic plate, CCD camera, or other type of electronic imaging device. Each of the spots from the lenslets is displaced on the image plane in proportion to the slope of the wavefront error. The resulting aberrated wavefront from the eye is analyzed by first finding the focus spot of each sub-aperture determined by the centroid of light distribution. By comparing the positions of corresponding focus spots in the real and reference patterns, the shifts of each focus spot in the x and y directions are calculated. The partial derivatives of the central sampling points of the deformed wavefront from the eye in both the x and y directions are determined from equations (3a) and (3b). The entire wavefront distribution is then reconstructed from the calculated partial derivatives of the aberrated wavefront using modal wavefront estimation. The tested wavefront, W (x,y), is assumed to be expressed by:

$$W(x, y) = \sum_{i=0}^{14} C_i Z_i(x, y) \quad (4)$$

where the $Z_i$ (x, y)'s are the Zernike polynomials up to fourth degree and the $C_i$'s are the corresponding coefficients for each mode. Using equations (3a) and (3b) the partial derivatives of W(x,y) take the form:

$$\frac{\partial W(x, y)}{\partial x} = \sum_{i=0}^{14} C_i \frac{\partial Z_i(x, y)}{\partial x} \quad (5a)$$

$$\frac{\partial W(x, y)}{\partial y} = \sum_{i=0}^{14} C_i \frac{\partial Z_i(x, y)}{\partial y} \quad (5b)$$

$$i = 0$$

A least squares fit is applied to the tested partial derivatives and the coefficients for the Zernike polynomial coefficients are obtained in matrix form $$C = (TM)(PQ) \quad (6)$$

where C is the coefficient column vector, PQ is the derivative column vector, and TM is a transformation matrix of dimension $14 \times 2N^2$, where $2N^2$ is the total number of measurements of derivatives. Thus, knowledge of the tested derivatives permits calculation of the Zernike coefficients, the entire wavefront distribution W (x,y), and therefore the contribution of individual Zernike modes. The final quantity has direct physical significance to the overall aberrations present in the eye because the individual Zernike modes represent a particular aberration, e.g., defocus, astigmatism, coma, etc., and thus their magnitudes are a measure of the contribution of the aberration adversely affecting vision.

The above discussion explicitly applies Zernike polynomials for wavefront decomposition. However, in practice the wavefront decomposition could be performed using Seidel aberration coefficients or any other appropriate set of basis functions.

Compensation of the aberrated wavefront may be achieved by use of a deformable mirror, a spatial light modulator (SLM), a micro-electromechanical membrane, a segmented micromirror, or appropriate wavefront compensator. A typical, commercially available deformable mirror consists of an aluminized glass faceplate with 37 PZT actuators mounted in a square array on the back surface. After computation of the wavefront error, voltages are applied to the appropriate actuators on the back surface of the deformable mirror to minimize or effectively null the aberrations of the system. In practice, the actuators are updated by correcting 10% of the error measured by the wavefront sensor in successive iterations. After the initial correction, the wavefront test is performed again, compared with the reference pattern of the ideal wavefront, the error is calculated, and voltages are applied to the appropriate PZT actuators of the deformable mirror. This procedure is repeated until a minimum in the root mean square (RMS) of the wavefront error is achieved.

c. Application of a Wavefront Sensor to an IOL Capable of Post-Implantation Power Modification The Shack-Hartmann wavefront sensor can be used to guide the modification of a power adjustable IOL in a human eye. After a power adjustable IOL has been implanted and sufficient time has passed for healing and refractive stabilization of the eye, the amount and type of aberrations in the eye can be evaluated with the Shack-Hartmann wavefront sensor, especially an adaptive optics system as described under section b. After reconstruction of the aberrated wavefront, the wavefront error is minimized by applying the necessary voltages to the actuators of the deformable mirror. Knowledge of the magnitude and location of the deformable mirror's adjustments can be used as reference for applying the light to the photoresponsive IOL to induce an appropriate amount of polymerization that minimizes the optical aberrations.

In another embodiment, use of a deformable mirror or other appropriate wavefront compensator is not absolutely required. Construction of the aberrated wavefront from measurement of the eye's optical aberrations using a Shack-Hartmann wavefront sensor will give sufficient information regarding the location and magnitude of the aberrations for the application of light. A treatment nomogram, i.e., a plot that defines the IOL's refractive response with respect to frequency, duration, and intensity of a stimulus such as irradiation in combination with the information of the extent of IOL polymerization necessary for achieving optimal visual acuity can be programmed into a spatial light modulator (SLM). A SLM with such programmed information can be used to deliver spatially differentiated stimuli that generate a desired amount of polymerization of RMC in an IOL.

The most common SLM is of the transmission configuration and is composed of liquid crystal material sandwiched between two ITO glass plates. A typical liquid crystal display (LCD) SLM consists of a 640×480 pixel array 25 $\mu$m on a side. Each individual pixel contains an approximate fill factor (the active area of each pixel) of 32% and is capable of 8-bit gray scale. Light of the desired intensity and diameter is brought incident upon the SLM. The pattern and the subsequent, spatially defined intensity of the output beam are determined by the user selected transmission state of each pixel. In this way, both the area and intensity of irradiation in a particular area is precisely controlled.

A second class of SLM devices that can be used in this proposed technology is a digital micromirror device (DMD) operating in reflection mode. A DMD is a pixelated, micromechanical spatial light modulator formed monolithically on a silicon substrate. Typical DMD chips have dimensions of 0.594×0.501 inches and the micromirrors are 13–17 $\mu$m square composed of silicon with a reflective coating. The micromirrors are arranged in an xy array, and the chips contains row drivers, column drivers, and timing circuitry. The addressing circuitry under each mirror pixel is a memory cell that drives two electrodes under the mirror with complimentary voltages. Depending on the state of the memory cell (a "1" or "0") each mirror is electrostatically attracted by a combination of the bias and address voltages to one of the other address electrodes. Physically the mirror can rotate ±10 degrees. A "1" in the memory causes the mirror to rotate ±10 degrees, while a "0" in the memory causes the mirror to rotate −10 degrees. A mirror rotated to +10 degrees reflects incoming light into the projection lens and onto the IOL through the eye. When the mirror is rotated −10 degrees, the reflected light misses the projection lens. The application of light to the IOL using a spatial light modulator could be accomplished by either irradiating the IOL with the predetermined intensity, duration, and placement in one application or the light could be applied in several doses with measurement of the evolving wavefront correction in the interim between irradiations.

d. Phase Contrast Variation of a Composition Comprising a Refraction Modulating Composition Examples 9, 10, 12, and 13 of this patent application described experiments geared towards correcting the aberration of defocus in these light adjustable IOLs. Defocus, astigmatism, and spherical aberration account for greater than 80% of all aberrations causing defective vision in people. Therefore, the ability to accurately correct these defects will greatly enhance visual acuity. The other, higher order aberrations are typically more complex in their spatial distribution and shape and require higher resolution modification (a spatial resolution on the order of microns) of the refraction properties of the light adjustable IOL as compared to the simple cases of astigmatism and defocus correction. To examine the resolution of the photorefractive materials composing the IOLs the following experiment was performed.

Thin films of the photorefractive composition were fabricated by first combining 60 wt % of diacetoxymethylsilyl endcapped polydimethylsiloxane (PDMS, $M_w$=36,000) matrix with 30 wt % methacryloxypropyldimethylsilyl endcapped polydimethylsiloxane ($M_w$=1000) macromer, 10 wt % methacryloxypropyldimethylsilyl endcapped polydimethylsiloxane ($M_w$=4,000) macromer, and 0.75 wt % (relative to the two macromers) of the photoinitiator, 2,2-dimethoxy-2-phenylacetophenone (DMPA). The composition was mixed thoroughly at room temperature for 5 minutes and degassed at 30 mtorr pressure for 15 minutes to remove any entrapped air. The material was then placed between two glass slides and allowed to cure at room temperature for 24 hours.

The irradiation was carried out using the 325 nm line of a He:Cd laser. The beam emanating from the laser was focused down to a 50 µm pinhole by a 75 mm focusing lens. A 125 mm lens was placed at a focal distance away from the pinhole to collimate the light producing a beam diameter of approximately 1.6 mm. Collimation of the beam was insured by monitoring the tilt angle of the fringes formed from a shearing plate interferometer placed in the beam. A 5000 lines/inch (period of ~5 µm) ruled grating was placed over the top surface of the sandwiched film and the photorefractive composition was exposed to the Talbot autoimage of the grating using 6.57 mW/cm$^2$ of collimated 325 nm light for 90 seconds.

Figure 10:
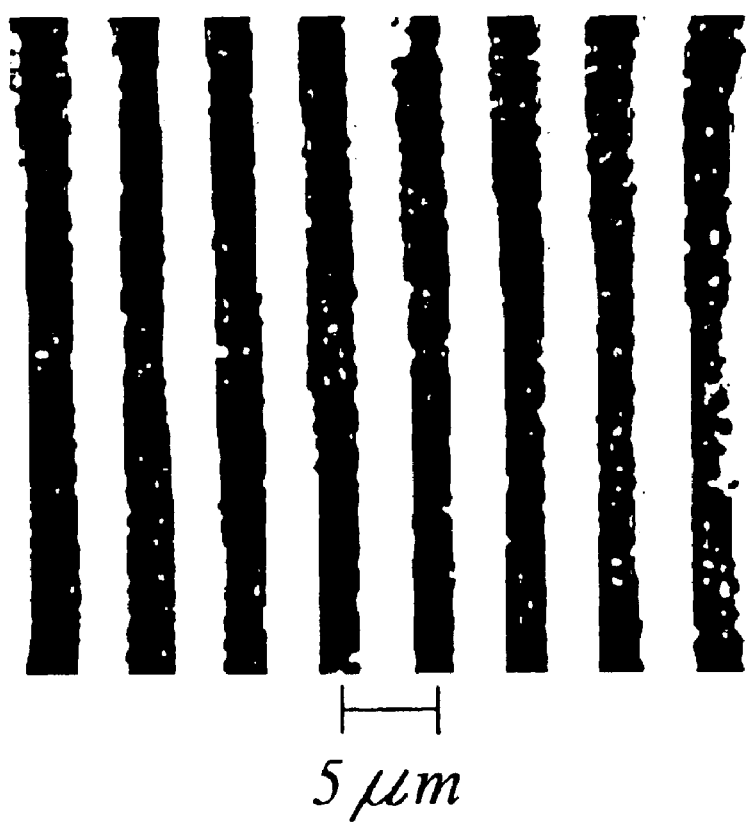
FIG. 10 is a photograph of a section of photopolymerized film.

FIG. 10 shows a microscope picture of the film after irradiation through the 5000 lines/inch mask. The magnification of the picture is approximately 125X. The alternating dark and light stripes running though the picture have a period of approximately 5 µm as determined by a calibrated microscope target. Therefore, the photoresponsive materials possess high spatial phase contrast.

The elements of the apparatus and the general features of the components are shown and described in relatively simplified and generally symbolic manner. Appropriate structural details and parameters for actual operation are available and known to those skilled in the art with respect to the conventional aspects of the process.

Although specific embodiments are disclosed herein, it is expected that persons skilled in the art can and will design alternative optical element and wavefront sensor systems that are within the scope of the following claims either literally or under the Doctrine of Equivalents.

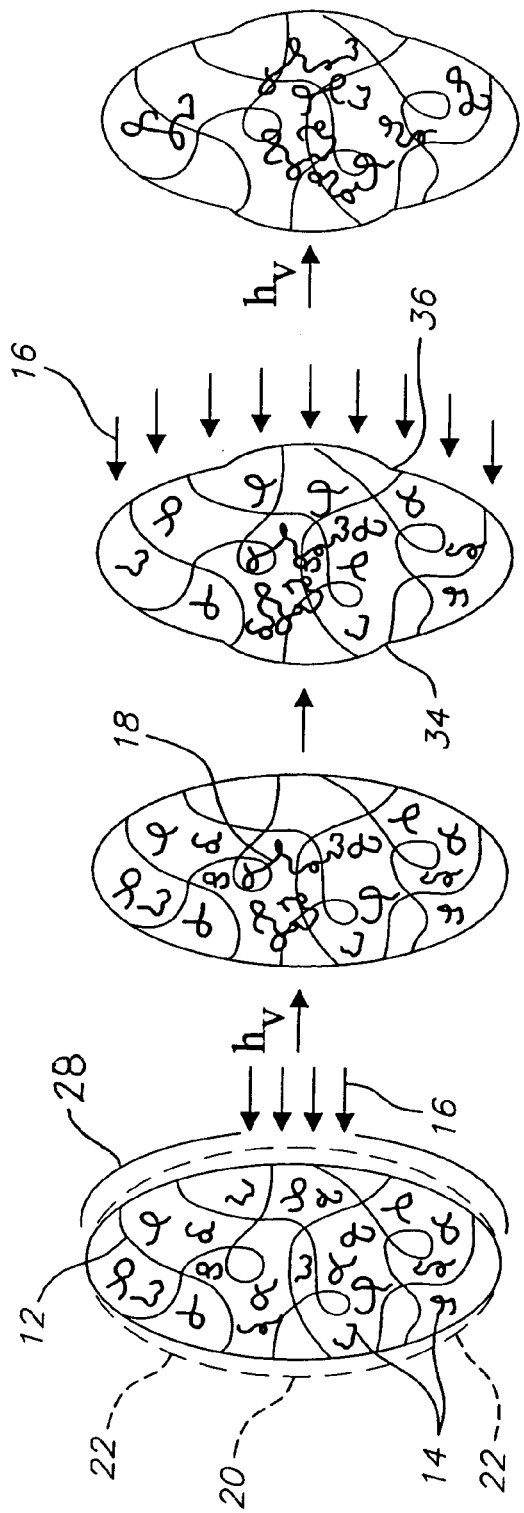

What is claimed is:

1. A system for correcting an aberration in an optical system comprising:
    an optical element inserted within the optical system and, wherein the optical element comprises a first polymer matrix and a refraction modulating composition dispersed therein wherein the refraction modulating composition is capable of stimulus-induced polymerization; and
    an optical measurement system for measuring the aberration in the inserted optical system and using a measurement of the aberration to determine the stimulus-induced polymerization.

2. The system of claim 1 wherein the optical measurement system comprises a wavefront sensor.

3. The system of claim 2 wherein the wave front sensor is a Shack-Hartmann wavefront sensor.

4. The system of claim 1 wherein the optical element is a lens.

5. The system of claim 4 wherein the optical element is an intraocular lens.

6. The system of claim 4 wherein the first polymer matrix is selected from the group consisting of polyacrylates, polymethacrylates, polyvinyls, and polysiloxanes.

7. The system of claim 5 wherein the refraction modulating composition includes a component selected from the group consisting of an acrylate, methacrylate, vinyl, siloxane, and phosphazine.

8. The system of claim 1 wherein the optical measurement system is an adaptive optics system, which comprises a wavefront sensor and a wavefront compensator.

9. The system of claim 8 wherein the wavefront compensator is selected from the group consisting of a deformable mirror, a micro-electromechanical membrane, and a segmented micromirror.

10. The system of claim 1 wherein the refraction modulation composition is capable of multiple stimulus-induced polymerizations.

11. A method comprising:
    inserting an optical element into an optical system, wherein the optical element has a refraction modulating composition dispersed therein;
    obtaining an optical measurement of the aberration of the optical system with the inserted optical element; and
    inducing an amount of polymerization of the refraction modulating composition, wherein at least one of the amount and spatial distribution of polymerization is determined by the optical measurement.

12. The method of claim 11 wherein the aberration measurement is converted to a set of basis functions selected from the group consisting of Zernike polynomials and Seidel polynomials.

13. The method of claim 11 wherein the aberration measurement is a measurement of at least one of the group consisting of defocus, astigmatism, coma, spherical, and higher order aberrations.

14. The method of claim 11 wherein the optical measurement is a wavefront measurement of the optical system.

15. The system of claim 11 wherein the optical measurement system comprises a wavefront sensor.

16. The method of claim 11 wherein the optical measurement system is an adaptive optics system, which comprises a wavefront sensor and a wavefront compensator.

17. The method of claim 16 wherein the wavefront compensator is selected from the group consisting of a deformable mirror, a micro-electromechanical membrane, and a segmented micromirror.

18. The method of claim 11 wherein at least one of the amount and spatial distribution of polymerization is induced by a spatial light modulator or a digital micromirror device.

19. The method of claim 11 wherein the optical element is disposed within an eye.

20. The method of claim 19 wherein the aberration measurement is a set of basis function selected from the group consisting of Zernike polynomials and Seidel polynomials describing the measured aberrations.

21. The method of claim 19 wherein the aberration measurement is a measurement of at least one of the group consisting of defocus, astigmatism, coma, spherical, and higher order aberrations.

22. The method of claim 19 wherein the optical measurement is a wavefront measurement of the eye.

23. The method of claim 19 wherein the optical measurement is obtained after an interval of time when the intraocular lens is implanted.

24. The system of claim 19 wherein the optical measurement system comprises a wavefront sensor.

25. The method of any of claims 15 and 24, wherein the wave front sensor is a Shack-Hartmann wavefront sensor.

26. The method of claim 19 wherein the optical measurement system is an adaptive optics system, which comprises a wavefront sensor and a wavefront compensator.

27. The method of claim 26 wherein the wavefront compensator is selected from the group consisting of a deformable mirror, a micro-electromechanical membrane, and a segmented micromirror.

28. The method of claim 20 wherein at least one of the amount and spatial distribution of polymerization is induced by a spatial light modulator or a digital micromirror device.

29. The method of claim 11 wherein the refraction modulation composition is capable of multiple stimulus-induced polymerizations, the method further comprising:

repeating the obtaining and inducing steps until the aberration of the optical element is corrected.

* * * * *

UNITED STATES PATENT AND TRADEMARK OFFICE
CERTIFICATE OF CORRECTION

PATENT NO. : 6,749,632 B2
DATED : June 15, 2004
INVENTOR(S) : Sandstedt et al.

It is certified that error appears in the above-identified patent and that said Letters Patent is hereby corrected as shown below:

Title page,
Item [56], References Cited, FOREIGN PATENT DOCUMENTS, delete
"EP    042384 A3    2/1992", insert
-- EP    0472384 A3    2/1992 --.
OTHER PUBLICATIONS,
"Canabal et al., Automatic processing in ..." reference, delete "No. 2", insert -- No. 25 --.
"Fouassier et al." reference, delete "Visible Lasers Lights", insert -- Visible Laser Lights --.
"Javitt et al.; Mechanism of hologram formation..." reference, delete "Status of Quality", insert -- Status and Quality --.
"Liang et al., Objective measurements of wave… " reference, delete "wavefront", insert -- wave-front --.
Insert the following:
-- VALDES-AGUILERA ET AL., Photopolymerization Studies Using Visible Light Photoinitiators; Macromolecules; 1992; pp. 541-547; Vol. 25, No. 2 ; American Chemical Society YANG, Z. ET AL., Activity and Stability of Enzymes Incorporated into Acrylic Polymers. Journal of American Chemical Society; 1995; pp. 4843-4850; Vol. 117; American Chemical Society YILGOR ET AL.; 14/Reactive Difunctional Siloxane Oligomers Synthesis and Characterization; American Chemical Society; 1985; pp. 161-174; American Chemical Society YU ET AL.; Fringe-orientation maps and fringe skeleton extraction by the two-dimensional derivative-sign binary-fringe method; APPLIED OPTICS; October 10, 1994; pp. 6873-6878; Vol. 33, No. 29; Optical Society of America ZHANG ET AL; Photorefractive Polymers and Composites; ADVANCED MATERIALS; 1996; pp. 111-125; Vol. 8, No. 2; VCH Verlagsgesellschaft mbH; Weinheim ZOBEL ET AL.; A Polysiloxane-Based Photorefractive Polymer with High Optical Gain and Diffraction Efficiency; ADVANCED MATERIALS; 1995; pp. 911-914; Vol. 7, No. 11; VCH Verlagsgesellschaft mbH; Weinheim --.

UNITED STATES PATENT AND TRADEMARK OFFICE
CERTIFICATE OF CORRECTION

PATENT NO.      : 6,749,632 B2
DATED           : June 15, 2004
INVENTOR(S)     : Sandstedt et al.

It is certified that error appears in the above-identified patent and that said Letters Patent is hereby corrected as shown below:

Drawings,
FIG. 5a, Sheet 5 of 10, delete and substitute with the attached page.

Column 26,
Line 22, delete "claim 4", insert -- claim 5 --.

Column 28,
Line 2, delete "wave front", insert -- wavefront --.

Signed and Sealed this

Seventh Day of February, 2006

JON W. DUDAS
*Director of the United States Patent and Trademark Office*